US006887694B1

(12) United States Patent
Rosenberg et al.

(10) Patent No.: US 6,887,694 B1
(45) Date of Patent: May 3, 2005

(54) DNA ENCODING A POLYPEPTIDE REQUIRED FOR BIOSYNTHESIS OF TA ANTIBIOTIC

(75) Inventors: Eugene Rosenberg, Givat Shmuel (IL); Eliora Ron, Tel Aviv (IL); Elisha Orr, Leicester (GB); Yossi Paitan, Rishon Le-Zion (IL)

(73) Assignee: Ramot At Tel Aviv University Ltd., Tel Aviv (IL)

( * ) Notice: Subject to any disclaimer, the term of this patent is extended or adjusted under 35 U.S.C. 154(b) by 626 days.

(21) Appl. No.: 09/710,262

(22) Filed: Nov. 10, 2000

Related U.S. Application Data

(63) Continuation-in-part of application No. 09/240,537, filed on Jan. 29, 1999, now abandoned.

(51) Int. Cl.[7] ............................................... C12N 9/00
(52) U.S. Cl. ................. 435/183; 435/320.1; 435/252.3; 435/252.33; 435/254.11; 435/419; 435/325; 536/23.1; 536/23.2; 536/23.7
(58) Field of Search .............................. 536/23.1, 23.2, 536/23.7; 435/320.1, 76, 252.3, 254.11, 419, 325, 252.33, 183

(56) References Cited

U.S. PATENT DOCUMENTS

| | | |
|---|---|---|
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |

OTHER PUBLICATIONS

Paitan et al. The First Gene in the Biosynthesis of the Polyketide Antibiotic TA of *Myxococcus xanthus* Codes for a Unique PKS Module Coupled to a Peptide Synthetase. J. Molecular Biology (Feb., 1999) 286: 465–474.*
Varon et al. Trans–acting regulation of antibiotic TA genes in *Myxococcus xanthus*. FEMS Microbiology Letters (1997) 155: 141–146.*

Tolchinsky et al. Use of Tn5lac to Study Expression of Genes Required for Production of the Antibiotic TA. Antimicrobial Agents and Chemotherapy (1992) 36(10): 2322–2327.*
Rosenberg, E., Vaks, B. and Zuckerberg. A Bactericidal action of an antibiotic produced by *Myxococcus xanthus*. Antimicrob. Agents. Chemother. 4:507–513 (1973).
Rosenberg E., Porter, J.M., Nathan, P.N., Manor, A. and Varon, M. Antibiotic TA: an adherent antibiotic. Bio/Technology. 2:796–799 (1984).
Varon et al., 1992. Antimicrobial Agents and Chemotherapy. 36(10):2316–2321.
Marshak et al, "Strategies for Protein Purification and Characterization. A laboratory course manual." CSHL Press, 1996.
Testoni et al, 1996, Blood 87:3822.
*PCR Protocols: A Guide to Methods and Applications*, Academic Press, San Diego, CA (1990).
Sembrook et al., *Molecular Cloning: A Laboratory Manual*, Cold Springs Harbor Laboratory, New York (1989. 1992).
Ausubel et al., *Current Protocols in Molecular Biology*, John Wiley and Sons, Baltimore, Maryland (1989).

* cited by examiner

*Primary Examiner*—P. Achutamurthy
*Assistant Examiner*—Kathleen Kerr
(74) *Attorney, Agent, or Firm*—G.E. Ehrlich Ltd.

(57) ABSTRACT

There is provided DNA sequences isolated from *Myxococcus xanthus* partially encoding a functional portion of a polypeptide component required for the synthesis of antibiotic TA. Also provided are purified, isolated and cloned DNA sequences encoding a polypeptide component required for postmodification of antibiotic TA and encoding a gene product involved in the regulation of the biosynthesis of antibiotic TA. A purified, isolated and cloned DNA sequence having a DNA sequence (seq. ID No:2 and 20) encoding a polypeptide component required for encoding the TA gene cluster and any mutations thereof is provided. Also provided are methods of using the TA genes for combinatorial genetics and of using the TA genes encoding for synthesis and modification or regulation of antibiotic TA.

7 Claims, 1 Drawing Sheet

SEQUENCE LISTING

```
<160> NUMBER OF SEQ ID NOS: 20

<210> SEQ ID NO 1
<211> LENGTH: 2392
<212> TYPE: PRT
<213> ORGANISM: Myxococcus xanthus

<400> SEQUENCE: 1

Val Asp Pro Ala Arg Leu Thr Arg Ala Trp Glu Gly Leu Leu Glu Arg
 1               5                  10                  15

Tyr Pro Leu Leu Ala Gly Ala Ile Arg Val Glu Gly Thr Glu Pro Val
            20                  25                  30

Ile Val Pro Ser Gly Gln Val Ser Ala Glu Val His Glu Val Pro Ser
        35                  40                  45

Val Ser Asp Ser Ala Leu Val Ala Thr Leu Arg Ala Ser Ala Lys Val
    50                  55                  60

Pro Phe Asp Leu Ala Cys Gly Pro Leu Ala Arg Leu His Leu Tyr Ser
65                  70                  75                  80

Arg Ser Glu His Glu His Val Leu Leu Leu Cys Phe His His Leu Val
                85                  90                  95

Leu Asp Gly Ala Ser Val Ala Pro Leu Leu Asp Ala Leu Arg Glu Arg
            100                 105                 110

Tyr Ala Gly Thr Glu Ala Lys Ala Gly Leu Leu Glu Val Pro Ile Val
        115                 120                 125

Ala Pro Tyr Arg Ala Ala Val Glu Trp Glu Gln Leu Ala Ile Gly Gly
    130                 135                 140

Asp Glu Gly Arg Arg His Leu Asp Tyr Trp Arg His Val Leu Ala Thr
145                 150                 155                 160

Pro Val Pro Pro Pro Leu Asn Leu Pro Thr Asp Arg Pro Arg Ser Ala
                165                 170                 175

Thr Gly Leu Asp Ser Glu Gly Ala Thr His Ser Gln Arg Val Pro Thr
            180                 185                 190

Glu Gln Ala Leu Arg Leu Arg Glu Phe Ala Arg Ala Gln Gln Val Ser
        195                 200                 205

Leu Pro Thr Val Leu Leu Gly Leu Tyr Tyr Ala Leu Leu His Arg His
    210                 215                 220

Thr Arg Gln Asp Asp Val Val Val Gly Ile Pro Thr Met Gly Arg Pro
225                 230                 235                 240
```

```
                                    -continued

Arg Ala Glu Leu Ala Thr Ala Ile Gly Tyr Phe Val Asn Val Met Ala
                245                 250                 255

Val Arg Ala Arg Gly Leu Gly Gln His Ser Phe Gly Ser Leu Leu Arg
            260                 265                 270

His Leu His Asp Ser Val Ile Asp Gly Leu Glu His Ala His Tyr Pro
        275                 280                 285

Phe Pro Arg Val Val Lys Asp Leu Arg Leu Ser Asn Gly Pro Glu Glu
    290                 295                 300

Ala Pro Gly Phe Gln Thr Met Phe Thr Phe Gln Ser Leu Gln Leu Thr
305                 310                 315                 320

Ser Ala Pro Pro Arg Pro Glu Pro Arg Ser Gly Gly Leu Pro Glu Leu
                325                 330                 335

Glu Pro Leu Asp Cys Val His Gln Gly Ala Tyr Pro Leu Glu Leu
            340                 345                 350

Glu Val Val Glu Gly Ala Lys Gly Leu Thr Leu His Phe Lys Tyr Asp
        355                 360                 365

Ala Arg Leu Tyr Glu Ala Asp Thr Val Glu Arg Met Ala Arg Gln Leu
    370                 375                 380

Leu Arg Ala Ala Asp Gln Val Ala Asp Gly Val Glu Ser Pro Leu Ser
385                 390                 395                 400

Ala Leu Ser Trp Leu Asp Asp Glu Glu Arg Arg Thr Leu Leu Arg Asp
                405                 410                 415

Trp Asn Ala Thr Ala Thr Pro Phe Leu Glu Asp Leu Gly Val His Glu
            420                 425                 430

Leu Phe Gln Arg Gln Ala Arg Glu Thr Pro Asp Ala Met Ala Val Ser
        435                 440                 445

Tyr Glu Gly His Ser Leu Ser Tyr Gln Ala Leu Asp Thr Arg Ser Arg
    450                 455                 460

Glu Ile Ala Ala His Leu Lys Ser Phe Gly Val Lys Pro Gly Ala Leu
465                 470                 475                 480

Val Gly Ile Tyr Leu Asp Arg Ser Ala Glu Leu Val Ala Ala Met Leu
                485                 490                 495

Gly Val Leu Ser Ala Gly Ala Ala Tyr Val Pro Leu Asp Pro Val His
            500                 505                 510

Pro Glu Asp Arg Leu Arg Tyr Met Leu Glu Asp Ser Gly Val Val Val
        515                 520                 525

Val Leu Ala Arg Gln Ala Ser Arg Asp Lys Val Ala Ala Ile Ala Gly
    530                 535                 540

Ala Ser Cys Lys Val Cys Val Leu Glu Asp Val Lys Ala Gly Ala Thr
545                 550                 555                 560

Ser Ala Pro Ala Gly Thr Ser Pro Asn Gly Leu Ala Tyr Val Ile Tyr
                565                 570                 575

Thr Ser Gly Ser Thr Gly Arg Pro Lys Gly Val Met Ile Pro His Arg
            580                 585                 590

Gly Val Val Asn Phe Leu Leu Cys Met Arg Arg Thr Leu Gly Leu Lys
        595                 600                 605

Arg Thr Asp Ser Leu Leu Ala Val Thr Thr Tyr Cys Phe Asp Ile Ala
    610                 615                 620

Ala Leu Glu Leu Leu Leu Pro Leu Cys Ala Gly Ala Gln Val Ile Ile
625                 630                 635                 640

Ala Ser Ala Glu Thr Val Arg Asp Ala Gln Ala Leu Lys Arg Ala Leu
                645                 650                 655

Arg Thr His Arg Pro Thr Leu Met Gln Ala Thr Pro Ala Thr Trp Thr
```

-continued

```
            660                665                670
Leu Leu Phe Gln Ser Gly Trp Glu Asn Ala Glu Arg Val Arg Ile Leu
            675                680                685
Cys Gly Gly Glu Ala Leu Pro Glu Ser Leu Lys Ala His Phe Val Arg
            690                695                700
Thr Ala Ser Asp Val Trp Asn Met Phe Gly Pro Thr Glu Thr Thr Ile
705                710                715                720
Trp Ser Thr Met Ala Lys Val Ser Ala Ser Arg Pro Val Thr Ile Gly
                725                730                735
Lys Pro Ile Asp Asn Thr Gln Val Tyr Val Leu Asp Asp Arg Met Gln
            740                745                750
Pro Val Pro Ile Gly Val Pro Gly Glu Leu Trp Ile Ala Gly Ala Gly
            755                760                765
Val Ala Cys Gly Tyr Leu Asn Arg Pro Ala Leu Thr Ala Glu Arg Phe
            770                775                780
Val Ser Asn Pro Phe Thr Pro Gly Thr Thr Leu Tyr Arg Thr Gly Asp
785                790                795                800
Leu Ala Arg Trp Arg Ala Asp Gly Glu Val Glu Tyr Leu Gly Arg Leu
                805                810                815
Asp His Gln Val Lys Val Arg Gly Phe Arg Ile Glu Met Gly Glu Ile
            820                825                830
Glu Ala Gln Leu Ala Gly His Pro Ser Val Lys Asn Cys Ala Val Val
            835                840                845
Ala Lys Glu Leu Asn Gly Thr Ser Gln Leu Val Ala Tyr Cys Gln Pro
            850                855                860
Ala Gly Thr Ser Phe Asp Glu Glu Ala Ile Arg Ala His Leu Arg Lys
865                870                875                880
Phe Leu Pro Asp Tyr Met Val Pro Ala His Val Phe Ala Val Asp Ala
                885                890                895
Ile Pro Leu Ser Gly Asn Gly Lys Val Asp Arg Gly Gln Leu Met Ala
                900                905                910
Arg Pro Val Val Thr Arg Arg Lys Thr Ser Ala Val His Ala Arg Ser
            915                920                925
Pro Val Glu Ala Thr Leu Val Glu Leu Trp Lys Asn Val Leu Gln Val
            930                935                940
Asn Glu Val Gly Val Glu Asp Arg Phe Phe Glu Val Gly Gly Asp Ser
945                950                955                960
Val Leu Ala Ala Val Leu Val Glu Glu Met Asn Arg Arg Phe Asp Thr
                965                970                975
Arg Leu Ala Val Thr Asp Leu Phe Lys Tyr Val Asn Ile Arg Asp Met
                980                985                990
Ala Arg His Met Glu Gly Ala Thr Ala Gln Ala Arg Thr Gly Ala Thr
            995                1000               1005
Glu Pro Ala Arg Glu Asp Thr Ala Ser Glu Arg Asp Tyr Glu Gly Ser
1010               1015               1020
Leu Ala Val Ile Gly Ile Ser Cys Gln Leu Pro Gly Ala Ala Asp Pro
1025               1030               1035               1040
Trp Arg Phe Trp Lys Asn Leu Arg Glu Gly Arg Asp Ser Val Val Ala
                1045               1050               1055
Tyr Arg His Glu Glu Leu Arg Glu Leu Gly Val Pro Glu Glu Val Leu
            1060               1065               1070
Arg Asp Ser Arg Tyr Val Ala Val Arg Ser Ser Ile Glu Asp Lys Glu
            1075               1080               1085
```

```
Cys Phe Asp Pro His Phe Phe Gly Leu Thr Ala Arg Asp Ala Ser Phe
    1090                1095                1100
Met Asp Pro Gln Phe Arg Leu Leu Met His Ala Trp Lys Ala Val
1105                1110                1115                1120
Glu Asp Ala Ala Thr Thr Pro Glu Arg Leu Gly Pro Cys Gly Val Phe
            1125                1130                1135
Met Thr Ala Ser Asn Ser Phe Tyr His Gln Gly Ser Pro Gln Phe Pro
            1140                1145                1150
Ala Asp Gly Gln Pro Val Leu Arg Thr Ala Glu Glu Tyr Val Leu Trp
        1155                1160                1165
Val Leu Ala Gln Ala Gly Ser Ile Pro Thr Met Val Ser Tyr Lys Leu
    1170                1175                1180
Gly Leu Lys Gly Pro Ser Leu Phe Val His Thr Asn Cys Ser Ser Ser
1185                1190                1195                1200
Leu Ser Ala Leu Tyr Val Ala Gln Gln Ala Ile Ala Ala Gly Asp Cys
                1205                1210                1215
Gln Thr Ala Leu Val Gly Ala Ala Thr Val Phe Pro Ser Ala Asn Leu
            1220                1225                1230
Gly Tyr Leu His Gln Arg Gly Leu Asn Phe Ser Ser Ala Gly Arg Val
        1235                1240                1245
Lys Ala Phe Asp Ala Ala Ala Asp Gly Met Ile Ala Gly Glu Gly Val
    1250                1255                1260
Ala Val Leu Val Val Lys Asp Ala Ala Ala Val Arg Asp Gly Asp
1265                1270                1275                1280
Pro Ile Tyr Cys Leu Val Arg Lys Val Gly Ile Asn Asn Asp Gly Gln
            1285                1290                1295
Asp Lys Val Gly Leu Tyr Ala Pro Ser Ala Thr Gly Gln Ala Glu Val
            1300                1305                1310
Ile Arg Arg Leu Phe Asp Arg Thr Gly Ile Asp Pro Ala Ser Ile Gly
        1315                1320                1325
Tyr Val Glu Ala His Gly Thr Gly Thr Leu Leu Gly Asp Pro Val Glu
    1330                1335                1340
Val Ser Ala Leu Ser Glu Ala Phe Arg Thr Phe Thr Asp Arg Arg Gly
1345                1350                1355                1360
Tyr Cys Arg Leu Gly Ser Val Lys Ser Asn Leu Gly His Leu Asp Thr
            1365                1370                1375
Val Ala Gly Leu Ala Gly Leu Ile Lys Thr Ala Leu Ser Leu Arg Gln
            1380                1385                1390
Gly Glu Val Pro Pro Thr Leu His Val Thr Gln Val Asn Pro Lys Leu
        1395                1400                1405
Glu Leu Thr Asp Ser Pro Phe Val Ile Ala Asp Arg Leu Ala Pro Trp
    1410                1415                1420
Pro Ser Leu Pro Gly Pro Arg Arg Ala Ala Val Ser Ala Phe Gly Leu
1425                1430                1435                1440
Gly Gly Thr Asn Thr His Ala Ile Leu Glu His Tyr Pro Arg Asp Ser
            1445                1450                1455
Arg Pro Arg Glu Arg Ser Gln Arg Ser Asn Ala Val Arg Ala Val Ala
            1460                1465                1470
Pro Phe Ser Ala Arg Thr Leu Glu Ala Leu Lys Asp Asn Leu Arg Ala
        1475                1480                1485
Leu Leu Asp Phe Leu Glu Asp Pro Ala Ser Ala Glu Val Ala Leu Ala
    1490                1495                1500
```

-continued

Asp Ile Thr Tyr Thr Leu Gln Val Gly Arg Val Ala Met Pro Glu Arg
1505                1510                1515                1520

Met Val Val Thr Ala Ser Thr Arg Asp Glu Leu Val Glu Gly Leu Arg
         1525                1530                1535

Arg Gly Ile Ala Thr Val Gly Gly Ala His Val Gly Thr Val Val Asp
         1540                1545                1550

Thr Ser Pro Ser Val Asp Ala Asp Ala Arg Ala Val Ala Glu Ala Trp
     1555                1560                1565

Ala Thr Gly Asp Ser Ile Asp Trp Asp Ser Leu His Gly Asp Val Lys
     1570                1575                1580

Pro Ala Arg Val Ser Leu Pro Thr Tyr Gln Phe Ala Lys Glu Arg Tyr
1585                1590                1595                1600

Gly Leu Ser Pro Ala His Ser Val Ala Asn Ser Ser Lys Thr His Pro
         1605                1610                1615

Asp Ala Gly Val Pro Leu Phe Val Pro Thr Trp Gln Pro Trp Ser Glu
         1620                1625                1630

Gly Ala Ser Asn Ala Ser Leu Ala Leu Arg His Leu Val Val Leu Cys
     1635                1640                1645

Glu Pro Leu Asp Ala Leu Gly Ala Glu Gly Ala Ser Ala Leu Ala Ser
     1650                1655                1660

Thr Leu Ala Asp Arg Arg Ile Glu Val Val Arg Thr Ser Ser Pro Ser
1665                1670                1675                1680

Ala Arg Leu Asp Ala Arg Phe Met Ala His Ala Ser Ala Val Phe Glu
         1685                1690                1695

Arg Val Lys Ala Leu Leu Ser Glu Arg Leu Thr Ala Pro Val Thr Leu
         1700                1705                1710

Gln Val Leu Val Pro Glu Glu Arg Asp Ala Leu Ala Leu Ser Gly Leu
     1715                1720                1725

Gly Ser Leu Leu Arg Ser Val Ser Gln Glu Asn Pro Leu Val Arg Gly
     1730                1735                1740

Gln Leu Ile Arg Val Gln Gly Ser Val Ser Ala Ser Ala Leu Val Asp
1745                1750                1755                1760

Val Leu Val Lys Ser Ala Arg Ala Gly Asp Val Thr Asp Ser Arg Tyr
         1765                1770                1775

His Ala Gly Gln Leu Ser Arg Cys Glu Trp Arg Glu Ala Arg Val Ala
         1780                1785                1790

Lys Gly Asp Ala Ser Arg Phe Trp Arg Glu Asp Gly Val Tyr Val Ile
     1795                1800                1805

Ser Gly Gly Thr Gly Ala Leu Ala Arg Leu Phe Val Ala Glu Ile Gly
     1810                1815                1820

Lys Arg Ala Thr Arg Ala Thr Val Ile Leu Val Ala Arg Ala Ser Ser
1825                1830                1835                1840

Ala Glu Ala Val Asp Gly Gly Asn Gly Leu Arg Val Arg His Leu Pro
         1845                1850                1855

Val Asp Val Thr Gln Pro Asn Asp Val Asn Ala Phe Val Ala Thr Val
         1860                1865                1870

Leu Arg Glu His Gly Arg Ile Asp Gly Val Ile His Ala Ala Gly Ile
     1875                1880                1885

Arg Arg Asp Asn Tyr Leu Leu Asn Lys Pro Val Ala Glu Met Gln Ala
     1890                1895                1900

Val Leu Ala Pro Lys Val Val Gly Leu Val Asn Leu Asp His Ala Thr
1905                1910                1915                1920

Arg Glu Leu Pro Leu Asp Phe Phe Val Thr Phe Ser Ser Leu Ala Ala

-continued

```
              1925             1930             1935
Phe Gly Asn Ala Gly Gln Ser Asp Tyr Ala Ala Ala Asn Gly Phe Met
        1940             1945             1950

Asp Gly Phe Ala Glu Ser Arg Ala Ala Leu Val Asn Ala Gly Gln Arg
    1955             1960             1965

Gln Gly Arg Thr Val Ser Ile Arg Trp Pro Leu Trp Glu Asn Gly Gly
    1970             1975             1980

Met Gln Leu Asp Ser Arg Ser Arg Glu Val Leu Met Gln Arg Thr Gly
1985             1990             1995             2000

Met Ala Ala Leu Gly Asp Glu Ala Gly Leu Gly Ala Phe Tyr Arg Ala
        2005             2010             2015

Leu Glu Leu Gly Ser Pro Gly Val Ala Val Trp Thr Gly Glu Ala Gln
        2020             2025             2030

Arg Phe Arg Glu Leu Ser Val Ser Val Ser Pro Ala Pro Pro Pro His
        2035             2040             2045

Gln Val Ala Leu Asp Ala Val Val Ser Ile Thr Glu Lys Val Glu Thr
        2050             2055             2060

Lys Leu Lys Ala Leu Phe Ser Glu Val Thr Arg Tyr Glu Glu Arg Arg
2065             2070             2075             2080

Ile Asp Ala Arg Gln Pro Met Glu Arg Tyr Gly Ile Asp Ser Ile Ile
        2085             2090             2095

Ile Thr Gln Met Asn Gln Ala Leu Glu Gly Pro Tyr Asn Ala Leu Ser
        2100             2105             2110

Lys Thr Leu Phe Phe Glu Tyr Arg Thr Leu Ala Glu Val Ser Gly Tyr
        2115             2120             2125

Leu Ala Glu His Arg Ala Glu Glu Ser Ala Lys Trp Val Ala Ala Pro
        2130             2135             2140

Gly Glu Asn Ser Ser Ser Val Ile Gln Glu Ala Arg Pro Pro Arg Ala
2145             2150             2155             2160

Asp Ala Thr His Arg Ala Pro Arg Ala Asp Glu Pro Ile Ala Val Ile
            2165             2170             2175

Gly Met Ser Gly Arg Tyr Pro Gly Ala Glu Asn Leu Thr Glu Phe Trp
        2180             2185             2190

Glu Arg Leu Ser Arg Gly Asp Asp Cys Ile Thr Glu Ile Pro Pro Glu
    2195             2200             2205

Arg Trp Ser Leu Asp Gly Phe Phe Tyr Pro Asp Lys Lys His Ala Ala
    2210             2215             2220

Ala Arg Gly Met Ser Tyr Ser Lys Trp Gly Gly Phe Leu Gly Gly Phe
2225             2230             2235             2240

Ala Asp Phe Asp Pro Leu Phe Phe Asn Ile Ser Pro Arg Glu Ala Thr
        2245             2250             2255

Ser Met Asp Pro Gln Glu Arg Leu Phe Leu Gln Ser Cys Trp Glu Val
        2260             2265             2270

Leu Glu Asp Ala Gly Tyr Thr Arg Asp Ser Leu Ala Gln Arg Phe Gly
        2275             2280             2285

Ser Ala Val Gly Val Phe Ala Gly Ile Thr Lys Thr Gly Tyr Glu Leu
        2290             2295             2300

Tyr Gly Ala Glu Leu Glu Gly Arg Asp Ala Ser Val Arg Pro Tyr Thr
2305             2310             2315             2320

Ser Phe Ala Ser Val Ala Asn Arg Val Ser Tyr Leu Leu Asp Leu Lys
            2325             2330             2335

Gly Pro Ser Met Pro Val Asp Thr Met Cys Ser Ala Ser Leu Thr Ala
        2340             2345             2350
```

```
Val His Met Ala Cys Glu Ala Leu Gln Arg Gly Ala Cys Val Met Ala
    2355                2360                2365

Ile Ala Gly Gly Val Asn Leu Tyr Val His Pro Ser Ser Tyr Val Ser
    2370                2375                2380

Leu Ser Gly Gln Gln Met Leu Ser
2385                2390

<210> SEQ ID NO 2
<211> LENGTH: 7178
<212> TYPE: DNA
<213> ORGANISM: Myxococcus xanthus

<400> SEQUENCE: 2
gtcgacccgg cgaggctgac ccgggcctgg gaaggactgc tcgaacggta tccgctgctc      60
gctggcgcga ttcgcgtcga aggcacggag ccggtcatcg tccccagtgg gcaggtctcc     120
gccgaggtcc acgaggttcc atcggtctcc gattcagcac tggtggcgac cctgcgcgcc     180
tccgcgaagg tgccattcga tctcgcctgt ggaccgctcg ctcggctgca cctgtactcg     240
cggtcggagc acgagcatgt cctgctgctg tgcttccacc acctggtgct cgatggggca     300
tccgtggcgc ccttgctcga cgccctccgg gagcgttacg ccgggaccga ggcgaaggcg     360
gggctgctcg aggttccgat cgtcgctcct taccgcgccg ccgtgagtg ggagcagctc      420
gccattggag gcgatgaggg acggcgccac ctcgactact ggcggcacgt gttggccacg     480
cccgttcctc cgccgttgaa tcttccaacg gaccggcctc gctccgccac ggggctggac     540
tcggagggag caacgcactc gcagagggtg cccaccgagc aagcattgcg actgcgcgag     600
ttcgctcggg cacagcaagt gagcctgccg accgtcctgc tcgggctcta ctacgccttg     660
cttcatcggc acacgcgcca ggacgacgtg gtggtcggca tccccaccat ggggcggccc     720
cgggcggaac tggcgacggc gattgggtac ttcgtcaacg tgatggccgt gcgcgcgcgg     780
ggcctggggc agcactcgtt cggctcgctg ctgcgccacc tccacgactc ggtcatcgat     840
ggcctggagc atgcccacta tcccttcccg cgagtggtga aggacctccg gctgtcgaat     900
gggcccgagg aggcgcctgg cttccagacg atgttcacct tccagagcct gcaactgacg     960
agcgctccgc caaggccgga gcccaggtcg ggcgggttgc cggagcttga ccgctcgac    1020
tgcgtccatc aggaaggcgc ctacccgctg gagcttgaag tggtggaggg cgccaagggc    1080
ctcacgctgc atttcaagta cgacgcgcgg ctgtacgagg cggacacggt cgaacggatg    1140
gcgcgtcagt tgttgcgcgc cgcggaccag gtcgcggatg gggtggagtc tccgctgagc    1200
gcactgtcgt ggctcgacga cgaagagcgc cgcacgcttc tccgcgactg gaatgccacg    1260
gccacgccgt tcctcgagga cctgggcgtt cacgagctct tccagcggca ggcccgggag    1320
accccagacg ccatggctgt gagctacgag gggcactcgc tcagctatca ggcgctggat    1380
acgcggagcc gcgagattgc ggcgcacctg aagagcttcg gcgtcaagcc tggggcgctc    1440
gtgggcatct acctggaccg gtccgcggag ctggtggcgg cgatgctggg tgtgctgtcc    1500
gctggcgcgg cctacgtacc cctggacccg gtgcaccccg aggaccggct gcggtacatg    1560
ctggaggaca gtggcgtggt ggtcgtgctg gcccgtcagg cctcgcggga caaggtcgcc    1620
gccattgccg gagcctcctg caaggtgtgc gtgctggagg acgtcaaggc tggagccacg    1680
tccgcgccgg cgggaaccctc accgaacgga cttgcctacg tcatctacac gtccgggagc    1740
acgggccggc ccaagggcgt gatgattccc catcgcgggg tggtcaactt cctcctgtgc    1800
atgcgcagga cgctgggcct gaagcgcacg gattcgctgt tggcggtcac gacgtactgc    1860
```

-continued

```
ttcgacatcg cggcgctcga gctcctgctt ccgctgtgtg cggggcgca ggtcatcatc    1920 gcgtcggcgg agacggttcg ggatgcgcag gcgttgaagc gggcgctgcg cacccatcgg    1980
cccacgttga tgcaggcgac gcccgcgacc tggacactgt tgttccagtc tggctgggag    2040
aacgccgagc gggttcgaat cctctgcggt ggagaagcgc tgccggagtc gctcaaggcc    2100
cacttcgttc gcaccgcgag cgacgtgtgg aacatgttcg ggcccaccga gacgaccatc    2160
tggtcgacga tggcgaaggt ctcggcctcg cgtccggtca ccattggaaa gccgatcgac    2220
aacacgcagg tctacgtgct ggacgaccgg atgcagccgg tgcccatcgg tgtgccgggc    2280
gagctgtgga ttgcgggcgc gggcgtggcc tgcggttacc tcaaccggcc ggcgctgacc    2340
gccgagcgct tcgtttccaa tccgttcacg ccgggcacga cgctctaccg gacgggggac    2400
ctggcgcgct ggcgcgctga cggtgaggtt gagtacctgg ggcggctcga ccaccaggtg    2460
aaggtgcgcg gcttccgcat cgagatgggg gagattgaag cgcagttggc cgggcatccc    2520
agcgtgaaga actgtgccgt ggtggccaag gagctgaacg gcacctcgca gctcgtcgcc    2580
tactgtcagc ccgcgggaac gagcttcgat gaggaagcca tccgtgcaca cctgcggaag    2640
ttcctccccg actacatggt ccccgcgcac gtcttcgcgg tggatgcgat tccgctgtcg    2700
ggcaatggca aggtggaccg gggccagctg atggccaggc cggtggtcac ccggcggaag    2760
acatccgcgg tccatgcccg ttcgcctgtt gaggccaccc tcgtcgagct gtggaagaac    2820
gtgctccagg tcaacgaggt gggtgtcgag gatcgcttct tcgaagtggg ggggactcc     2880 gtgctggccg ccgtgctggt ggaggagatg aaccggcgct tcgacacgcg gctcgccgtc    2940
accgacctgt tcaagtacgt caatattcgc gacatggcgc gccacatgga gggcgcgacg    3000
gcgcaagccc gtactggggc caccgagccg gctcgcgagg acaccgcgtc ggagcgtgac    3060
tacgagggca gcctggccgt catcggcatc tcctgtcagt tgcccggagc cgcggacccc    3120
tggcgcttct ggaagaacct gcgagagggc agggacagcg tggtggcgta ccgccatgag    3180
gaactgcgcg agctgggcgt gcccgaggag gtcctccgcg attcccgtta cgtcgcggtc    3240
cggtcgtcca tcgaagacaa ggagtgcttc gacccgcatt tcttcggtct gacggcgcgg    3300
gacgcgtcct tcatggaccc gcagttccga ctgttgctga tgcacgcctg gaaggcagtg    3360
gaagacgcgg cgacgacgcc tgagcgcctg ggaccgtgcg gcgtcttcat gacggccagc    3420
aacagcttct atcaccaggg ctcgccgcaa tttcctgcgg acgggcagcc ggtcctccgc    3480
accgccgaaa aatacgtgct gtgggtgctg gcccaggcag gctccatccc gacgatggtt    3540
tcstacaagc tcggcttgaa ggggccgagc ctgttcgtcc acaccaactg ctcgtcatcc    3600
ctgtccgcgc tgtacgtggc tcagcaggcc atcgcagcgg gagactgcca gacggcgctg    3660
gtgggggccg ccacggtctt cccttcggcg aacttgggtt atctgcacca gcgggggctc    3720
aacttctcca gcgcggggcg ggtcaaggcc ttcgacgccg cggcggacgg catgattgcc    3780
ggtgaaggtg tcgccgtgct ggtggtgaag gacgccgcag cggcggtgcg cgatggcgac    3840
ccaatctact gcctcgtgcg gaaggtgggg atcaacaacg acggccagga caaggtgggt    3900
ttatacgccc cgagcgccac cgggcaggcg gaggtcatcc ggcgtctgtt cgaccggacc    3960
ggcatcgacc ctgcatcgat tggctacgtc gaggcccatg gcaccggaac cttgctgggt    4020
gaccctgtcg aggtctccgc gctgagcgaa gccttccgga ccttcaccga ccggcgcggg    4080
tactgccggc tgggctcggt gaagtcgaac ctgggccatc tggacacagt ggctggactg    4140
gctgggctca tcaagacggc gctgagcctg cggcagggcg aagttcctcc gacgctccat    4200
```

-continued

```
gtgacccagg tgaatccgaa gctcgagctg acggattcgc cgttcgtcat cgccgaccgt    4260
ttggcgccgt ggccgtccct gccgggaccg aggcgggcgg ccgtgagtgc gttcggcctt    4320
ggcgggacga ataccacgc cattctcgaa cactacccgc gcgactcccg cccacgggag     4380
aggagccagc ggtcgaacgc agtccgtgcg gtggctccat tctcggcgcg caccctggag    4440
gcgttgaagg acaacctccg cgcgctgctc gacttcctgg aggacccggc gtccgcggag    4500
gtggcgctcg cggacatcac ctacacgttg caggtcggcc gggtcgcgat gcctgagcgg    4560
atggtggtga ctgcgtcgac gcgcgacgaa ttggtggagg gactgcggcg aggcatcgcg    4620
acggtgggcg gtgcccacgt gggaacggtg gtcgatacgt cacccagcgt ggatgccgat    4680
gctcgggcag ttgcggaggc gtgggcgacg ggcgactcga ttgactggga ttcgctgcac    4740
ggtgacgtga agcccgcccg tgtcagcctg cccacgtatc agttcgcgaa ggagcgctac    4800
gggttgtcgc ccgcgcactc cgtggcgaat tcctccaaga cgcatcctga cgcgggtgtc    4860
ccgctcttcg ttccgacctg gcagccgtgg tctgagggcg cgtcaaatgc ctcgttggcg    4920
ctccggcacc tggtggtgtt gtgcgagcct cttgatgcgc tgggggctga aggtgcctcc    4980
gcgctggcga gcacgctcgc ggacaggcgc atcgaagtgg tcaggacgtc cagcccaagt    5040
gcgcggctgg acgcgcggtt catggcgcat gcctcggcgg tcttcgaacg cgtcaaggcg    5100
ctgctgtcga agcgtctgac cgctcctgtg acattgcagg tgctggtgcc agaggagcgg    5160
gatgcgctgg cactgagtgg cctggggagc ctgctgcgtt cggtgtcgca ggagaatccg    5220
ttggtccggg ggcagctcat ccgcgtccag ggaagcgtct ccgcatcggc gctggtggac    5280
gttctggtga agtccgcgcg cgccggtgac gtcaccgatt cgcggtacca cgcgggccag    5340 cttttctcgct gtgagtggcg cgaggcacgt gtcgccaagg gggacgcatc ccgcttctgg    5400
cgcgaagacg gcgtctatgt gatttcagga ggaaccggcg ccctggcccg gctgttcgtc    5460
gccgaaatcg ggaagcgcgc gacgcggggcc accgtcattc tggttgcccg cgcatcctcg    5520
gcggaggcgg tggacggtgg gaacgggctg cgcgtgcggc accttcccgt ggatgtcacc    5580
caaccgaacg acgtgaacgc ctttgtcgct acggtgctgc cgaacacgg gcgcatcgac    5640 ggtgtcatcc atgcggcggg catccgccgt gacaactacc tgctcaacaa gccggtggcg    5700
gaaatgcagg cggtgctcgc gcccaaggtg gtgggggctcg tcaacctgga ccacgccacc    5760
cgcgagctgc ccctggattt cttcgtcacg ttctcgtccc tggccgcgtt tggaaacgcc    5820
ggtcagtcgg actacgcggc ggccaatggc ttcatggacg gattcgcgga gtcccgagcg    5880
gcgctcgtga acgccggaca gcggcagggc cggacggtgt ccatccgttg gccgctctgg    5940
gagaacggcg ggatgcagct cgactcacgg agccgtgagg tcttgatgca gcggaccggg    6000
atggccgcgc tgggagacga agcgggactg ggggcgttct accggcgct ggaactgggc     6060 tccctggtg tcgcggtgtg gacggggggag gcccagaggt ttcgtgaact ctccgtgagt   6120
gtttcgcccc caccgcctcc gcatcaggtg gcgttggacg ccgtggtgtc catcaccgag    6180
aaggtcgaga cgaagctgaa ggcgctcttc agcgaggtca cgcgatacga agagcgccgc    6240
atcgatgccc gccagccgat ggagcgctat ggcatcgact ccatcatcat cacgcagatg    6300
aaccaagccc tcgaagggcc gtacaacgcc ctctcgaaga cgctgttctt cgaataccgg    6360 acgctcgcg aagtcagcgg gtatctggcc gagcaccgcg cggaagagag cgcgaagtgg     6420
gtggcggcac ctggagagaa ttcgtcttcc gtcatccagg aggccaggcc gccacgtgcg    6480
gatgcgacgc accgggcgcc tcgcgccgac gagcccatcg ccgtcattgg catgagcggc    6540
cgttatcccg gggcggagaa cctgacggag ttctgggagc gcctgagccg cggtgacgac    6600
```

-continued

```
tgcatcaccg agattccgcc agagcgctgg tcgttggacg ggttcttcta cccggacaag    6660
aagcacgccg ccgcgcgggg gatgagctac agcaagtggg gcggcttcct cggcggcttc    6720
gctgacttcg acccgctgtt cttcaacatc tcgccgcgtg aggcgacgag catggacccg    6780
caggagcgct tgttcctgca gagctgctgg gaggtcctgg aggacgcggg gtacacccgg    6840
gacagcctgg cccagcgctt tggcagcgcg gtgggcgttt tcgcgggaat cacgaagacg    6900
ggctacgaac tctacggcgc ggagctggaa ggacgagatg cctcggtccg gccctatacg    6960
tcgtttgcgt ctgttgccaa ccgcgtctcg tatctgctcg acctgaaggg gccgagcatg    7020
cccgtggaca ccatgtgctc ggcctcgctg acagccgtcc acatggcttg cgaggcgctg    7080
caacgaggcg cctgcgtcat ggccatcgcg ggtggagtga atctctacgt ccacccgtcg    7140
agctacgtca gcctgtccgg gcagcagatg ctgtcgac                             7178
```

<210> SEQ ID NO 3
<211> LENGTH: 785
<212> TYPE: PRT
<213> ORGANISM: Myxococcus xanthus

<400> SEQUENCE: 3

```
Met Lys Val Val Asn Lys Leu Leu Glu Lys Leu Pro Asp Val Ala
 1               5                  10                  15

Gly Lys Val Pro Asp Val Lys Leu Gln Asp Gln Asp Ile Lys Val Pro
                20                  25                  30

Leu Ala Gln Gly Thr Phe Thr Glu Glu Lys Ile Leu Pro Pro Lys Leu
         35                  40                  45

Ala Met His Gly Phe Thr Leu Ser Phe Glu Ala Thr Gly Glu Ala Ser
     50                  55                  60

Ile Arg Asn Phe Asn Ser Leu Gly Asp Val Asp Glu Asn Gly Ile Ile
 65                  70                  75                  80

Gly Glu Pro Ser Pro Glu Ser Ala Glu Pro Gly Pro Arg Pro Gln Leu
                 85                  90                  95

Leu Leu Gly Ser Asp Ile Gly Trp Met Arg Tyr Gln Val Ser Ala Arg
            100                 105                 110

Val Lys Ala Ala Val Ser Ala Ser Leu Ser Phe Leu Ala Ser Glu Asn
        115                 120                 125

Gln Thr Glu Leu Ser Val Thr Leu Ser Asp Tyr Arg Ala His Pro Leu
    130                 135                 140

Gly Gln Asn Met Arg Glu Ala Val Arg Ser Asp Leu Ser Glu Leu Arg
145                 150                 155                 160

Leu Met Gln Ala Thr Asp Leu Ala Lys Leu Thr Thr Gly Asp Ala Val
                165                 170                 175

Ala Trp His Val Arg Gly Ala Leu His Thr Arg Leu Glu Leu Asn Trp
            180                 185                 190

Ala Asp Ile Phe Pro Thr Asn Leu Asn Arg Leu Gly Phe Leu Arg Gly
        195                 200                 205

Asn Glu Leu Leu Ala Leu Lys Thr Ser Ala Lys Ala Gly Leu Ser Ala
    210                 215                 220

Arg Val Ser Leu Thr Asp Asp Tyr Gln Leu Ser Phe Ser Arg Pro Arg
225                 230                 235                 240

Ala Gly Arg Ile Gln Val Ala Val Arg Lys Val Lys Ser His Glu Gln
                245                 250                 255

Ala Leu Ser Ala Gly Leu Gly Ile Thr Val Glu Leu Leu Asp Pro Ala
            260                 265                 270
```

-continued

```
Thr Val Lys Ala Gln Leu Gly Gln Leu Leu Glu Ala Leu Leu Gly Pro
    275                 280                 285
Val Leu Arg Asp Leu Val Lys Lys Gly Thr Thr Ala Val Glu Ile Met
290                 295                 300
Asp Gly Leu Val Asp Lys Ala Ser Lys Ala Lys Leu Asp Asp Asn Gln
305                 310                 315                 320
Lys Lys Val Leu Gly Leu Val Leu Glu Arg Leu Gly Ile Asp Pro Gln
                325                 330                 335
Leu Ala Asp Pro Ala Asn Leu Pro Gln Ala Trp Ala Asp Phe Lys Ala
            340                 345                 350
Arg Val Ala Glu Ser Leu Glu Asn Ala Val Arg Thr Gln Val Ala Glu
        355                 360                 365
Gly Phe Glu Tyr Glu Tyr Leu Arg Leu Ser Glu Thr Ser Thr Leu Leu
    370                 375                 380
Glu Val Val Glu Asp Val Thr Ala Met Arg Phe His Glu Ser Leu
385                 390                 395                 400
Leu Lys Gly Asn Leu Val Glu Leu Leu Lys Trp Met Lys Ser Leu Pro
                405                 410                 415
Ala Gln Gln Ser Glu Phe Glu Leu Arg Asn Tyr Leu His Ala Thr Thr
            420                 425                 430
Leu Thr Arg Gln Gln Ala Ile Gly Phe Ser Leu Gly Leu Gly Ser Phe
        435                 440                 445
Glu Leu Leu Lys Ala Lys Asn Val Ser Lys Gln Ser Trp Val Thr Gln
    450                 455                 460
Glu Asn Phe Gln Gly Ala Arg Arg Met Ala Phe Leu Gly Arg Arg Gly
465                 470                 475                 480
Tyr Glu Asp Lys Leu Leu Gly Thr Arg Gly Gln Trp Val Val Asp Leu
                485                 490                 495
Lys Ala Asp Met Thr Arg Phe Ser Pro Thr Pro Val Ala Ser Asp Phe
            500                 505                 510
Gly Tyr Gly Leu His Leu Met Leu Trp Gly Arg Gln Lys Lys Leu Ser
        515                 520                 525
Arg Lys Asp Leu Gln Gln Ala Val Asp Asp Ala Val Val Trp Gly Val
    530                 535                 540
Leu Asp Ala Lys Asp Ala Ala Thr Val Ile Ser Thr Met Gln Glu Asp
545                 550                 555                 560
Met Gly Lys His Pro Ile Glu Thr Arg Leu Glu Leu Lys Met Ala Asp
                565                 570                 575
Asp Ser Phe Arg Ala Leu Val Pro Arg Ile Gln Thr Leu Glu Leu Ser
            580                 585                 590
Arg Phe Ser Arg Ala Leu Ala Arg Ala Leu Pro Trp Ser Glu Gln Leu
        595                 600                 605
Pro Arg Ala Ser Ala Glu Phe Arg Arg Ala Val Tyr Ala Pro Ile Trp
    610                 615                 620
Glu Ala Tyr Leu Arg Glu Val Gln Gln Gly Ser Leu Met Leu Asn
625                 630                 635                 640
Asp Leu Ser Pro Ser Arg Ala Ala Gln Ile Ala Lys Trp Tyr Phe Gln
                645                 650                 655
Lys Asp Pro Thr Val Arg Asp Leu Gly Lys Asp Leu Gln Leu Ile Glu
            660                 665                 670
Ser Glu Trp Arg Pro Gly Gly Asn Phe Ser Phe Ala Glu Val Ile
        675                 680                 685
```

```
Ser Lys Asn Pro Asn Thr Leu Met Arg Cys Arg Asn Phe Val Ser Gly
    690                 695                 700

Met Val Arg Leu Arg Arg Ala Ile Asp Glu Arg Lys Ala Pro Asp Glu
705                 710                 715                 720

Leu Arg Thr Val Phe Gly Glu Leu Glu Gly Met Trp Thr Thr Gly Phe
                725                 730                 735

His Leu Arg Ala Ala Gly Ser Leu Leu Ser Asp Leu Ala Gln Ser Thr
                740                 745                 750

Pro Leu Gly Leu Ala Gly Val Glu Arg Thr Leu Thr Val Arg Val Ala
                755                 760                 765

Asp Ser Glu Glu Gln Leu Val Phe Ser Thr Ala Arg Ser Thr Gly Ala
770                 775                 780

Ala
785

<210> SEQ ID NO 4
<211> LENGTH: 529
<212> TYPE: PRT
<213> ORGANISM: Myxococcus xanthus

<400> SEQUENCE: 4

Met Pro Ser Gly Cys Tyr Gly Ala Ala Ser Ala Phe Val Leu Pro Pro
1               5                   10                  15

Leu Pro Ala Met Pro Gln Ala Pro Ser Asp Val Ser Gln Val Leu Leu
                20                  25                  30

Pro Phe Gly Gly Leu Val Gly Arg Glu Val Asp Leu Asp Ala Phe Leu
            35                  40                  45

Gln Thr Leu Met Asp Arg Ile Ala Ile Thr Leu Gln Ala Asp Arg Gly
    50                  55                  60

Thr Leu Trp Leu Leu Asp Pro Ala Arg Arg Glu Leu Phe Ser Arg Ala
65              70                  75                  80

Ala His Leu Pro Glu Val Ser Gln Ile Arg Val Lys Leu Gly Gln Gly
                85                  90                  95

Val Ala Gly Thr Val Ala Lys Ala Gly His Ala Ile Asn Val Pro Asp
                100                 105                 110

Pro Arg Gly Glu Gln Arg Phe Phe Ala Asp Ile Asp Arg Met Thr Gly
            115                 120                 125

Tyr Arg Thr Thr Ser Leu Leu Ala Val Pro Leu Arg Asp Gly Asp Gly
    130                 135                 140

Ala Leu Tyr Gly Val Leu Gln Val Leu Asn Arg Gly Glu Asp Arg
145             150                 155                 160

Phe Thr Asp Glu Asp Thr Gln Arg Leu Thr Ala Ile Ala Ser Gln Val
                165                 170                 175

Ser Thr Ala Leu Gln Ser Thr Ser Leu Tyr Gln Glu Leu Gln Arg Ala
                180                 185                 190

Lys Glu Gln Pro Gln Val Pro Val Gly Tyr Phe Phe Asn Arg Ile Ile
            195                 200                 205

Gly Glu Ser Pro Gln Leu Gln Ala Ile Tyr Arg Leu Val Arg Lys Ala
    210                 215                 220

Ala Pro Thr Asp Ala Thr Val Leu Leu Arg Gly Glu Ser Gly Ser Gly
225             230                 235                 240

Lys Glu Leu Phe Ala Arg Ala Val His Val Asn Gly Pro Arg Arg Asp
                245                 250                 255

Gln Pro Phe Ile Lys Val Asp Cys Ala Ala Leu Pro Ala Thr Leu Ile
            260                 265                 270
```

-continued

```
Glu Asn Glu Leu Phe Gly His Glu Arg Gly Ala Phe Thr Gly Ala Asp
            275                 280                 285

His Arg Val Pro Gly Lys Phe Glu Ala Ala Ser Gly Gly Thr Val Phe
        290                 295                 300

Ile Asp Glu Ile Gly Glu Leu Pro Leu Pro Val Gln Gly Lys Leu Leu
305                 310                 315                 320

Arg Val Ile Gln Asp Arg Glu Phe Glu Arg Val Gly Gly Thr Gln Ala
                325                 330                 335

Val Lys Val Asp Val Arg Ile Val Ala Ala Thr His Arg Asp Leu Ala
            340                 345                 350

Arg Met Val Ala Glu Gly Arg Phe Arg Glu Asp Leu Tyr Tyr Arg Ile
        355                 360                 365

Lys Val Val Glu Val Val Leu Pro Pro Leu Arg Glu Arg Gly Ala Glu
    370                 375                 380

Asp Ile Glu Arg Leu Ala Arg His Phe Val Ala Ala Val Ala Arg Arg
385                 390                 395                 400

His Arg Leu Thr Pro Pro Arg Leu Ser Ala Ala Val Glu Arg Leu
                405                 410                 415

Lys Arg Tyr Arg Trp Pro Gly Asn Val Arg Glu Leu Glu Asn Cys Ile
            420                 425                 430

Glu Ser Ala Val Val Leu Cys Glu Gly Glu Ile Leu Glu Glu His Leu
        435                 440                 445

Pro Leu Pro Asp Val Asp Arg Ala Ala Leu Pro Pro Ala Ala Ala
450                 455                 460

Gln Gly Val Asn Ala Pro Thr Ala Pro Ala Pro Leu Asp Ala Gly Leu
465                 470                 475                 480

Leu Pro Leu Ala Glu Val Arg Arg His Ile Leu Arg Val Leu Asp
                485                 490                 495

Ala Val Lys Gly Asn Arg Thr Ala Ala Ala Arg Val Leu Ala Ile Gly
            500                 505                 510

Arg Asn Thr Leu Ala Arg Lys Leu Lys Glu Tyr Gly Leu Gly Asp Glu
        515                 520                 525

Pro

<210> SEQ ID NO 5
<211> LENGTH: 292
<212> TYPE: PRT
<213> ORGANISM: Myxococcus xanthus

<400> SEQUENCE: 5

Met Arg Ala Ser Gln Ala Glu Ala Pro His Ser Arg Arg Leu Thr Met
  1               5                  10                  15

Glu Val Arg Phe His Gly Val Arg Gly Ser Ile Ala Val Ser Gly Ser
             20                  25                  30

Arg Ile Gly Gly Asn Thr Ala Cys Val Glu Val Thr Ser Gln Gly His
         35                  40                  45

Arg Leu Ile Leu Asp Ala Gly Thr Gly Ile Arg Ala Leu Gly Glu Ile
     50                  55                  60

Met Met Arg Glu Gly Ala Pro Gln Glu Ala Thr Leu Phe Phe Ser His
 65                  70                  75                  80

Leu His Trp Asp His Val Gln Gly Phe Pro Phe Thr Pro Ala Trp
             85                  90                  95

Leu Pro Thr Ser Glu Leu Thr Leu Tyr Gly Pro Gly Ala Asn Gly Ala
            100                 105                 110
```

```
Gln Ala Leu Gln Ser Glu Leu Ala Ala Gln Met Gln Pro Leu His Phe
            115                 120                 125

Pro Val Pro Leu Ser Thr Met Arg Ser Arg Met Asp Phe Arg Ser Ala
130                 135                 140

Leu His Ala Arg Pro Val Glu Val Gly Pro Phe Arg Val Thr Pro Ile
145                 150                 155                 160

Asp Val Pro His Pro Gln Gly Cys Leu Ala Tyr Arg Leu Glu Ala Asp
            165                 170                 175

Gly His Ser Phe Val Tyr Ala Thr Asp Val Glu Val Arg Val Gln Glu
            180                 185                 190

Leu Ala Pro Glu Val Gly Arg Leu Phe Glu Gly Ala Asp Val Leu Cys
            195                 200                 205

Leu Asp Ala Gln Tyr Thr Pro Asp Glu Tyr Glu Gly Arg Lys Gly Val
            210                 215                 220

Ala Lys Lys Gly Trp Gly His Ser Thr Met Met Asp Ala Ala Gly Val
225                 230                 235                 240

Ala Gly Leu Val Gly Ala Arg Arg Leu Cys Leu Phe His His Asp Pro
            245                 250                 255

Ala His Gly Asp Asp Met Leu Glu Asp Met Ala Glu Gln Ala Arg Ala
            260                 265                 270

Leu Phe Pro Val Cys Glu Pro Ala Arg Glu Gly Gln Arg Leu Val Leu
            275                 280                 285

Gly Arg Ala Ala
    290

<210> SEQ ID NO 6
<211> LENGTH: 168
<212> TYPE: PRT
<213> ORGANISM: Myxococcus xanthus

<400> SEQUENCE: 6

Met Pro Gly Pro Arg Cys Ala Glu Asn Asp Trp Val Ala Leu Leu Val
1               5                   10                  15

Arg Val Asn His Glu Lys Val Ala Ala Gln Leu Gly Lys His Gly
            20                  25                  30

Tyr Glu Phe Phe Leu Pro Thr Tyr Thr Pro Pro Lys Ser Ser Gly Val
            35                  40                  45

Lys Ala Lys Leu Pro Leu Phe Pro Gly Tyr Leu Phe Cys Arg Tyr Gln
    50                  55                  60

Pro Leu Asn Pro Tyr Arg Ile Val Arg Ala Pro Gly Val Ile Arg Leu
65                  70                  75                  80

Leu Gly Gly Asp Ala Gly Pro Glu Ala Val Pro Ala Gln Glu Leu Glu
                85                  90                  95

Ala Ile Arg Arg Val Ala Asp Ser Gly Val Ser Ser Asn Pro Cys Asp
            100                 105                 110

Tyr Leu Arg Val Gly Gln Arg Val Arg Ile Ile Glu Gly Pro Leu Thr
            115                 120                 125

Gly Leu Glu Gly Ser Leu Val Thr Ser Lys Ser Gln Leu Arg Phe Ile
    130                 135                 140

Val Ser Val Gly Leu Leu Gln Arg Ser Val Ser Val Glu Val Ser Ala
145                 150                 155                 160

Glu Gln Leu Glu Pro Ile Thr Asp
                165
```

<210> SEQ ID NO 7
<211> LENGTH: 79
<212> TYPE: PRT
<213> ORGANISM: Myxococcus xanthus

<400> SEQUENCE: 7

Met Asp Lys Arg Ile Ile Phe Asp Ile Val Thr Ser Ser Val Arg Glu
1               5                   10                  15

Val Val Pro Glu Leu Glu Ser His Pro Phe Glu Pro Glu Asp Asp Leu
            20                  25                  30

Val Gly Leu Gly Ala Asn Ser Leu Asp Arg Ala Glu Ile Val Asn Leu
        35                  40                  45

Thr Leu Glu Lys Leu Ala Leu Asn Ile Pro Arg Val Glu Leu Ile Asp
    50                  55                  60

Ala Lys Thr Ile Gly Gly Leu Val Asp Val Leu His Ala Arg Leu
65                  70                  75

<210> SEQ ID NO 8
<211> LENGTH: 420
<212> TYPE: PRT
<213> ORGANISM: Myxococcus xanthus

<400> SEQUENCE: 8

Met Gly Pro Val Gly Ile Glu Ala Met Asn Ala Tyr Cys Gly Ile Ala
1               5                   10                  15

Arg Leu Asp Val Leu Gln Leu Ala Thr His Arg Gly Leu Asp Thr Ser
            20                  25                  30

Arg Phe Ala Asn Leu Leu Met Glu Glu Lys Thr Val Pro Leu Pro Tyr
        35                  40                  45

Glu Asp Pro Val Thr Tyr Gly Val Asn Ala Ala Arg Pro Ile Leu Asp
    50                  55                  60

Gln Leu Thr Ala Ala Glu Arg Asp Ser Ile Glu Leu Leu Val Ala Cys
65                  70                  75                  80

Thr Glu Ser Ser Phe Asp Phe Gly Lys Ala Met Ser Thr Tyr Leu His
                85                  90                  95

Gln His Leu Gly Leu Ser Arg Asn Cys Arg Leu Ile Glu Leu Lys Ser
            100                 105                 110

Ala Cys Tyr Ser Gly Val Ala Gly Leu Gln Met Ala Val Asn Phe Ile
        115                 120                 125

Leu Ser Gly Val Ser Pro Gly Ala Lys Ala Leu Val Val Ala Ser Asp
    130                 135                 140

Leu Ser Arg Phe Ser Ile Ala Glu Gly Gly Asp Ala Ser Thr Glu Asp
145                 150                 155                 160

Trp Ser Phe Ala Glu Pro Ser Ser Gly Ala Gly Ala Val Ala Met Leu
                165                 170                 175

Val Ser Asp Thr Pro Arg Val Phe Arg Val Asp Val Gly Ala Asn Gly
            180                 185                 190

Tyr Tyr Gly Tyr Glu Val Met Asp Thr Cys Arg Pro Val Ala Asp Ser
        195                 200                 205

Glu Ala Gly Asp Ala Asp Leu Ser Leu Leu Ser Tyr Leu Asp Cys Cys
    210                 215                 220

Glu Asn Ala Phe Arg Glu Tyr Thr Arg Val Pro Ala Ala Asn Tyr
225                 230                 235                 240

Ala Glu Ser Phe Gly Tyr Leu Ala Phe His Thr Pro Phe Gly Gly Met
                245                 250                 255

Val Lys Gly Ala His Arg Thr Met Met Arg Lys Phe Ser Gly Lys Asn

-continued

```
                    260                 265                 270
Arg Gly Asp Ile Glu Ala Asp Phe Gln Arg Arg Val Ala Pro Gly Leu
            275                 280                 285

Thr Tyr Cys Gln Arg Val Gly Asn Ile Met Gly Ala Thr Met Ala Leu
        290                 295                 300

Ser Leu Leu Gly Thr Ile Asp His Gly Asp Phe Ala Thr Ala Lys Arg
305                 310                 315                 320

Ile Gly Cys Phe Ser Tyr Gly Ser Gly Cys Ser Ser Glu Phe Phe Ser
                325                 330                 335

Gly Val Val Thr Glu Glu Gly Gln Gln Arg Gln Arg Ala Leu Gly Leu
            340                 345                 350

Gly Glu Ala Leu Gly Arg Arg Gln Gln Leu Ser Met Pro Asp Tyr Asp
        355                 360                 365

Ala Leu Leu Lys Gly Asn Gly Leu Val Arg Phe Gly Thr Arg Asn Ala
370                 375                 380

Glu Leu Asp Phe Gly Val Val Gly Ser Ile Arg Pro Gly Gly Trp Gly
385                 390                 395                 400

Arg Pro Leu Leu Phe Leu Ser Ala Ile Arg Asp Phe His Arg Asp Tyr
                405                 410                 415

Gln Trp Ile Ser
            420
```

<210> SEQ ID NO 9
<211> LENGTH: 325
<212> TYPE: PRT
<213> ORGANISM: Myxococcus xanthus

<400> SEQUENCE: 9

```
Met Ser Ser Val Ala Thr Ala Val Pro Leu Thr Ala Arg Asp Ser Ala
  1               5                  10                  15

Val Ser Arg Arg Leu Arg Ile Thr Pro Ser Met Cys Gly Gln Thr Ser
            20                  25                  30

Leu Phe Ala Gly Gln Ile Gly Asp Trp Ala Trp Asp Thr Val Ser Arg
        35                  40                  45

Leu Cys Gly Thr Asp Val Leu Thr Ala Thr Asn Ala Ser Gly Ala Pro
 50                  55                  60

Thr Tyr Leu Ala Phe Tyr Tyr Phe Arg Ile Arg Gly Thr Pro Ala Leu
 65                  70                  75                  80

His Pro Gly Ala Leu Arg Phe Gly Asp Thr Leu Asp Val Thr Ser Lys
                85                  90                  95

Ala Tyr Asn Phe Gly Ser Glu Ser Val Leu Thr Val His Arg Ile Cys
            100                 105                 110

Lys Thr Ala Glu Gly Gly Ala Pro Glu Ala Asp Ala Phe Gly His Glu
        115                 120                 125

Glu Leu Tyr Glu Gln Pro Gln Pro Gly Arg Ile Tyr Ala Glu Thr Phe
    130                 135                 140

Asn Arg Trp Ile Thr Arg Ser Asp Gly Lys Ser Asn Glu Ser Leu Ile
145                 150                 155                 160

Lys Ser Ser Pro Val Gly Phe Gln Tyr Ala His Leu Pro Leu Leu Pro
                165                 170                 175

Asp Glu Tyr Ser Pro Arg Arg Ala Tyr Gly Asp Ala Arg Ala Arg Gly
            180                 185                 190

Thr Phe His Asp Val Asp Ser Ala Glu Tyr Arg Leu Thr Val Asp Arg
        195                 200                 205
```

```
Phe Pro Leu Arg Tyr Ala Val Asp Val Ile Arg Asp Val Asn Gly Val
    210                 215                 220

Gly Leu Ile Tyr Phe Ala Ser Tyr Phe Ser Met Val Asp Trp Ala Ile
225                 230                 235                 240

Trp Gln Leu Ala Arg His Gln Gly Arg Ser Glu Gln Ala Phe Leu Ser
                245                 250                 255

Arg Val Val Leu Asp Gln Gln Leu Cys Phe Leu Gly Asn Ala Ala Leu
            260                 265                 270

Asp Thr Thr Phe Asp Ile Asp Val Gln His Trp Glu Arg Val Gly Gly
        275                 280                 285

Gly Glu Glu Leu Phe Asn Val Lys Met Arg Glu Gly Ala Gln Gly Arg
    290                 295                 300

Asp Ile Ala Val Ala Thr Val Lys Val Arg Phe Asp Ala Ala Ser Glu
305                 310                 315                 320

Gly Gly Arg Arg Gly
                325

<210> SEQ ID NO 10
<211> LENGTH: 83
<212> TYPE: PRT
<213> ORGANISM: Myxococcus xanthus

<400> SEQUENCE: 10

Met Thr Asp Glu Gln Ile Arg Gly Val Val His Gln Ser Ile Val Arg
  1               5                  10                  15

Val Leu Pro Arg Val Arg Ser Asn Glu Ile Ala Gly His Leu Asn Leu
             20                  25                  30

Arg Glu Leu Gly Ala Asp Ser Val Asp Arg Val Glu Ile Leu Thr Ser
         35                  40                  45

Ile Leu Asp Ser Leu Arg Leu Gln Lys Thr Pro Leu Ala Lys Phe Ala
     50                  55                  60

Asp Ile Arg Asn Ile Asp Ala Leu Val Ala Phe Leu Ala Gly Glu Val
 65                  70                  75                  80

Ala Gly Gly

<210> SEQ ID NO 11
<211> LENGTH: 374
<212> TYPE: PRT
<213> ORGANISM: Myxococcus xanthus

<400> SEQUENCE: 11

Met Met Gln Glu Arg Gly Val Ala Leu Pro Phe Glu Asp Pro Val Thr
  1               5                  10                  15

Asn Ala Val Asn Ala Ala Arg Pro Ile Leu Asp Ala Met Ser Pro Glu
             20                  25                  30

Ala Arg Glu Arg Ile Glu Leu Leu Val Thr Ser Ser Glu Ser Gly Val
         35                  40                  45

Asp Phe Ser Lys Ser Ile Ser Ser Tyr Ala His Glu His Leu Gly Leu
     50                  55                  60

Ser Arg His Cys Arg Phe Leu Glu Val Lys Gln Ala Cys Tyr Ala Ala
 65                  70                  75                  80

Thr Gly Ala Leu Gln Leu Ala Leu Gly Tyr Ile Ala Ser Gly Val Ser
                 85                  90                  95

Pro Gly Ala Lys Ala Leu Val Ile Ala Thr Asp Val Thr Leu Val Asp
            100                 105                 110

Glu Ser Gly Leu Tyr Ser Glu Pro Ala Met Gly Thr Gly Gly Val Ala
```

```
            115                 120                 125
Val Leu Leu Gly Asp Glu Pro Arg Val Met Lys Met Asp Leu Gly Ala
        130                 135                 140

Phe Gly Asn Tyr Ser Tyr Asp Val Phe Asp Thr Ala Arg Pro Ser Pro
145                 150                 155                 160

Glu Ile Asp Ile Gly Asp Val Asp Arg Ser Leu Phe Thr Tyr Leu Asp
                165                 170                 175

Cys Leu Lys His Ser Phe Ala Ala Tyr Gly Arg Arg Val Asp Gly Val
            180                 185                 190

Asp Phe Val Ser Thr Phe Asp Tyr Leu Ala Met His Thr Pro Phe Ala
        195                 200                 205

Gly Leu Val Lys Ala Gly His Arg Lys Met Met Arg Glu Leu Thr Pro
    210                 215                 220

Cys Asp Val Asp Glu Ile Glu Ala Asp Phe Gly Arg Arg Val Lys Pro
225                 230                 235                 240

Ser Leu Gln Tyr Pro Ser Leu Val Gly Asn Leu Cys Ser Gly Ser Val
                245                 250                 255

Tyr Leu Ser Leu Cys Ser Ile Ile Asp Thr Ile Lys Pro Glu Arg Ser
            260                 265                 270

Ala Arg Val Gly Met Phe Ser Tyr Gly Ser Gly Cys Ser Ser Glu Phe
        275                 280                 285

Phe Ser Gly Val Ile Gly Pro Glu Ser Val Ser Ala Leu Ala Gly Leu
    290                 295                 300

Asp Ile Gly Gly His Leu Arg Gly Arg Gln Leu Thr Phe Asp Gln
305                 310                 315                 320

Tyr Val Glu Leu Leu Lys Glu Asn Leu Arg Cys Leu Val Pro Thr Lys
                325                 330                 335

Asn Arg Asp Val Asp Val Glu Arg Tyr Leu Pro Leu Val Thr Arg Thr
            340                 345                 350

Ala Ser Arg Pro Arg Met Leu Ala Leu Arg Arg Val Val Asp Tyr His
        355                 360                 365

Arg Gln Tyr Glu Trp Val
    370

<210> SEQ ID NO 12
<211> LENGTH: 171
<212> TYPE: PRT
<213> ORGANISM: Myxococcus xanthus

<400> SEQUENCE: 12

Met Asn Thr Pro Ser Leu Thr Asn Trp Pro Ala Arg Leu Gly Tyr Leu
1               5                   10                  15

Leu Ala Val Gly Gly Ala Trp Phe Ala Ala Asp Gln Val Thr Lys Gln
            20                  25                  30

Met Ala Arg Asp Gly Ala Lys Arg Pro Val Ala Val Phe Asp Ser Trp
        35                  40                  45

Trp His Phe His Tyr Val Glu Asn Arg Ala Gly Ala Phe Gly Leu Phe
    50                  55                  60

Ser Ser Phe Gly Glu Glu Trp Arg Met Pro Phe Phe Tyr Val Val Gly
65                  70                  75                  80

Ala Ile Cys Ile Val Leu Leu Ile Gly Tyr Tyr Phe Tyr Thr Pro Pro
                85                  90                  95

Thr Met Lys Leu Gln Arg Trp Ser Leu Ala Thr Met Ile Gly Gly Ala
            100                 105                 110
```

-continued

Leu Gly Asn Tyr Val Asp Arg Val Arg Leu Arg Tyr Val Val Asp Phe
        115                 120                 125

Val Ser Trp His Val Gly Asp Arg Phe Tyr Trp Pro Ser Phe Asn Ile
130                 135                 140

Ala Asp Thr Ala Val Val Val Gly Ala Ala Leu Met Ile Leu Glu Ser
145                 150                 155                 160

Phe Arg Glu Pro Arg Gln Gln Leu Ser Pro Gly
                165                 170

<210> SEQ ID NO 13
<211> LENGTH: 475
<212> TYPE: PRT
<213> ORGANISM: Myxococcus xanthus

<400> SEQUENCE: 13

Met Gly Thr Ser Glu Pro Val Glu Pro Asp His Ala Leu Ser Lys Pro
  1               5                  10                  15

Pro Pro Val Ala Pro Val Gly Ala Gln Ala Leu Pro Arg Gly Pro Ala
                 20                  25                  30

Met Pro Gly Ile Ala Gln Leu Met Met Leu Phe Leu Arg Pro Thr Glu
             35                  40                  45

Phe Leu Asp Arg Cys Ala Ala Arg Tyr Gly Asp Thr Phe Thr Leu Lys
         50                  55                  60

Ile Pro Gly Thr Pro Pro Phe Ile Gln Thr Ser Asp Pro Ala Leu Ile
 65                  70                  75                  80

Glu Val Ile Phe Lys Gly Asp Pro Asp Leu Phe Leu Gly Gly Lys Ala
                 85                  90                  95

Asn Asn Gly Leu Lys Pro Val Val Gly Glu Asn Ser Leu Leu Val Leu
            100                 105                 110

Asp Gly Lys Arg His Arg Arg Asp Arg Lys Leu Ile Met Pro Thr Phe
        115                 120                 125

Leu Gly Glu Arg Met His Ala Tyr Gly Ser Val Ile Arg Asp Ile Val
    130                 135                 140

Asn Ala Ala Leu Asp Arg Trp Pro Val Gly Lys Pro Phe Ala Val His
145                 150                 155                 160

Glu Glu Thr Gln Gln Ile Met Leu Glu Val Ile Leu Arg Val Ile Phe
                165                 170                 175

Gly Leu Glu Asp Ala Arg Thr Ile Ala Gln Phe Arg His His Val His
            180                 185                 190

Gln Val Leu Lys Leu Ala Leu Phe Leu Phe Pro Asn Gly Glu Gly Lys
        195                 200                 205

Pro Ala Ala Glu Gly Phe Ala Arg Ala Val Gly Lys Ala Phe Pro Ser
    210                 215                 220

Leu Asp Val Phe Ala Ser Leu Lys Ala Ile Asp Asp Ile Ile Tyr Gln
225                 230                 235                 240

Glu Ile Gln Asp Arg Ser Gln Asp Ile Ser Gly Arg Gln Asp Val
                245                 250                 255

Leu Ser Leu Met Met Gln Ser His Tyr Asp Asp Gly Ser Val Met Thr
            260                 265                 270

Pro Gln Glu Leu Arg Asp Glu Leu Met Thr Leu Leu Met Ala Gly His
        275                 280                 285

Glu Thr Ser Ala Thr Ile Ala Ala Trp Cys Val Tyr His Leu Cys Arg
    290                 295                 300

His Pro Asp Ala Met Gly Lys Leu Arg Glu Glu Ile Ala Ala His Thr
305                 310                 315                 320

-continued

```
Val Asp Gly Val Leu Pro Leu Ala Lys Ile Asn Glu Leu Lys Phe Leu
                325                 330                 335

Asp Ala Val Val Lys Glu Thr Met Arg Ile Thr Pro Val Phe Ser Leu
                340                 345                 350

Val Ala Arg Val Leu Lys Glu Pro Gln Thr Ile Gly Thr Thr Tyr
                355                 360                 365

Pro Ala Asn Val Val Leu Ser Pro Asn Ile Tyr Gly Thr His His Arg
                370                 375                 380

Ala Asp Leu Trp Gly Asp Pro Lys Val Phe Arg Pro Glu Arg Phe Leu
385                 390                 395                 400

Glu Glu Arg Val Asn Pro Phe His Tyr Phe Pro Phe Gly Gly Gly Ile
                405                 410                 415

Arg Lys Cys Ile Gly Thr Ser Phe Ala Tyr Tyr Glu Met Lys Ile Phe
                420                 425                 430

Val Ser Glu Thr Val Arg Arg Met Arg Phe Asp Thr Arg Pro Gly Tyr
                435                 440                 445

His Ala Lys Val Val Arg Arg Ser Asn Thr Leu Ala Pro Ser Gln Gly
                450                 455                 460

Val Pro Ile Ile Val Glu Ser Arg Leu Pro Ser
465                 470                 475

<210> SEQ ID NO 14
<211> LENGTH: 318
<212> TYPE: PRT
<213> ORGANISM: Myxococcus xanthus

<400> SEQUENCE: 14

Met Val Asp Ser Val Ser Lys Gln Ala Arg Arg Lys Val Phe Leu Phe
1               5                   10                  15

Ser Gly Gln Gly Thr Gln Ser Tyr Phe Met Ala Lys Glu Leu Phe Asp
                20                  25                  30

Thr Gln Thr Gly Phe Lys Arg Gln Leu Leu Glu Leu Asp Glu Gln Phe
                35                  40                  45

Lys Gln Arg Leu Gly His Ser Ile Leu Glu Arg Ile Tyr Asp Ala Arg
                50                  55                  60

Ala Ala Arg Leu Asp Pro Leu Asp Asp Val Leu Val Ser Phe Pro Ala
65                  70                  75                  80

Ile Phe Met Ile Glu His Ala Leu Ala Arg Leu Leu Ile Asp Arg Gly
                85                  90                  95

Ile Gln Pro Asp Ala Val Gly Ala Ser Met Gly Glu Val Ala Ala
                100                 105                 110

Ala Ala Ile Ala Gly Ala Ile Ser Val Asp Ala Val Ala Leu Val
                115                 120                 125

Ala Ala Gln Ala Gln Leu Phe Ala Arg Thr Ala Pro Arg Gly Gly Met
                130                 135                 140

Leu Ala Val Leu His Glu Leu Glu Ala Cys Arg Gly Phe Thr Ser Val
145                 150                 155                 160

Ala Arg Asp Gly Glu Val Ala Ala Ile Asn Tyr Pro Ser Asn Phe Val
                165                 170                 175

Leu Ala Ala Asp Glu Ala Gly Leu Gly Arg Ile Gln Gln Glu Leu Ser
                180                 185                 190

Gln Arg Ser Val Ala Phe His Arg Leu Pro Val Arg Tyr Pro Phe His
                195                 200                 205

Ser Ser His Leu Asp Pro Leu Arg Glu Glu Tyr Arg Ser Arg Val Arg
```

-continued

```
            210                 215                 220
Ala Asp Ser Leu Thr Trp Pro Arg Ile Pro Met Tyr Ser Cys Thr Thr
225                 230                 235                 240

Ala Asn Arg Val His Asp Leu Arg Ser Asp His Phe Trp Asn Val Val
                245                 250                 255

Arg Ala Pro Ile Gln Leu Tyr Asp Thr Val Leu Gln Leu Glu Gly Gln
                260                 265                 270

Gly Gly Cys Asp Phe Ile Asp Val Gly Pro Ala Ala Ser Phe Ala Thr
                275                 280                 285

Ile Ile Lys Arg Ile Leu Ala Arg Asp Ser Thr Ser Arg Leu Phe Pro
290                 295                 300

Leu Leu Ser Pro Ser Pro Ala Ser Thr Gly Ser Ser Met Gly
305                 310                 315

<210> SEQ ID NO 15
<211> LENGTH: 330
<212> TYPE: PRT
<213> ORGANISM: Myxococcus xanthus

<400> SEQUENCE: 15

Met Thr Glu Ala Pro Ala Pro Arg Ala Pro Ala Gln Val Pro Pro Pro
1               5                   10                  15

Pro Ser Ser Pro Trp Ala Leu His Thr Arg Gly Ala Ala Ser Ala Pro
                20                  25                  30

Val Asn Ala Arg Lys Ala Ala Leu Phe Pro Gly Gln Gly Ser Gln Glu
            35                  40                  45

Arg Gly Met Gly Ala Ala Leu Phe Asp Glu Phe Pro Asp Leu Thr Asp
        50                  55                  60

Ile Ala Asp Ala Ile Leu Gly Tyr Ser Ile Lys Arg Leu Cys Leu Glu
65                  70                  75                  80

Asp Pro Gly Lys Glu Leu Ala Gln Thr Gln Phe Thr Gln Pro Ala Leu
                85                  90                  95

Tyr Val Val Asn Ala Leu Ser Tyr Leu Lys Arg Leu Arg Glu Gly Ala
                100                 105                 110

Glu Gln Pro Ala Phe Val Ala Gly His Ser Leu Gly Glu Tyr Asn Ala
            115                 120                 125

Leu Leu Val Ala Gly Ala Phe Asp Phe Glu Thr Gly Leu Arg Leu Val
        130                 135                 140

Lys Arg Arg Gly Glu Leu Met Ser Gly Ala Ser Gly Gly Thr Met Ala
145                 150                 155                 160

Ala Val Val Gly Cys Asp Ala Val Ala Val Glu Gln Val Leu Arg Asp
                165                 170                 175

Arg Gln Leu Thr Ser Leu Asp Ile Ala Asn Ile Asn Ser Pro Asp Gln
                180                 185                 190

Ile Val Val Ser Gly Pro Ala Gln Asp Ile Glu Arg Ala Arg Gln Cys
            195                 200                 205

Phe Val Asp Arg Gly Ala Arg Tyr Val Pro Leu Asn Val Arg Ala Pro
210                 215                 220

Phe His Ser Arg Tyr Met Gln Pro Ala Ala Ser Glu Phe Glu Arg Phe
225                 230                 235                 240

Leu Ser Gln Phe Gln Tyr Ala Pro Leu Arg Cys Val Val Ile Ser Asn
                245                 250                 255

Val Thr Gly Arg Pro Tyr Ala His Asp Asn Val Val Gln Gly Leu Ala
            260                 265                 270
```

-continued

```
Leu Gln Leu Arg Ser Pro Val Gln Trp Thr Ala Thr Val Arg Tyr Leu
        275                 280                 285

Leu Glu Gln Gly Val Glu Asp Phe Glu Glu Leu Gly Pro Gly Arg Val
    290                 295                 300

Leu Thr Arg Leu Ile Thr Ala Asn Lys Arg Gly Ala Pro Ala Pro Ala
305                 310                 315                 320

Thr Ala Pro Ala Lys Trp Ala Asn Ala
                325                 330

<210> SEQ ID NO 16
<211> LENGTH: 417
<212> TYPE: PRT
<213> ORGANISM: Myxococcus xanthus

<400> SEQUENCE: 16

Met Ser Thr Ser Pro Val Gln Glu Leu Val Ser Gly Phe Gly Val
1               5                   10                  15

Thr Ser Ala Ile Gly Gln Gly Ala Ala Ser Phe Thr Ser Ala Leu Leu
            20                  25                  30

Glu Gly Ala Ala Arg Phe Arg Val Met Glu Arg Pro Gly Arg Gln His
        35                  40                  45

Gln Ala Asn Gly Gln Thr Thr Ala His Leu Gly Ala Glu Ile Ala Ser
    50                  55                  60

Leu Ala Val Pro Glu Gly Val Thr Pro Gln Leu Trp Arg Ser Ala Thr
65                  70                  75                  80

Phe Ser Gly Gln Ala Ala Leu Val Thr Val His Glu Ala Trp Asn Ala
                85                  90                  95

Ala Arg Leu Gln Ala Val Pro Gly His Arg Ile Gly Leu Val Val Gly
            100                 105                 110

Gly Thr Asn Val Gln Gln Arg Asp Leu Val Leu Met Gln Asp Ala Tyr
        115                 120                 125

Arg Glu Arg Val Pro Phe Leu Arg Ala Ala Tyr Gly Ser Thr Phe Met
    130                 135                 140

Asp Thr Asp Leu Val Gly Leu Cys Thr Gln Gln Phe Ala Ile His Gly
145                 150                 155                 160

Met Ser Phe Thr Val Gly Gly Ala Ser Ala Ser Gly Leu Leu Ala Val
                165                 170                 175

Ile Gln Ala Ala Glu Ala Val Leu Ser Arg Lys Val Asp Val Cys Ile
            180                 185                 190

Ala Val Gly Ala Leu Met Asp Val Ser Tyr Trp Glu Cys Gln Gly Leu
        195                 200                 205

Arg Ala Met Gly Ala Met Gly Thr Asp Arg Phe Ala Arg Glu Pro Glu
    210                 215                 220

Arg Ala Cys Arg Pro Phe Asp Arg Glu Ser Asp Gly Phe Ile Phe Gly
225                 230                 235                 240

Glu Ala Cys Gly Ala Val Val Glu Ser Ala Glu His Ala Arg Arg
                245                 250                 255

Arg Gly Val Thr Pro Arg Gly Ile Leu Ser Gly Trp Ala Met Gln Leu
            260                 265                 270

Asp Ala Ser Arg Gly Pro Leu Ser Ser Ile Glu Arg Glu Ser Gln Val
        275                 280                 285

Ile Gly Ala Ala Leu Arg His Ala Asp Leu Ala Pro Glu Arg Val Asp
    290                 295                 300

Tyr Val Asn Pro His Gly Ser Gly Ser Arg Gln Gly Asp Ala Ile Glu
305                 310                 315                 320
```

```
Leu Gly Ala Leu Lys Ala Cys Gly Leu Thr His Ala Arg Val Asn Thr
                325                 330                 335

Thr Lys Ser Ile Thr Gly His Gly Leu Ser Ser Ala Gly Ala Val Gly
            340                 345                 350

Leu Ile Ala Thr Leu Val Gln Leu Glu Gln Gly Arg Leu His Pro Ser
        355                 360                 365

Leu Asn Leu Val Asp Pro Ile Asp Ser Ser Phe Arg Trp Val Gly Ala
    370                 375                 380

Thr Ala Glu Ala Gln Ser Leu Gln Asn Ala Leu Val Leu Ala Tyr Gly
385                 390                 395                 400

Phe Gly Gly Ile Asn Thr Ala Val Ala Val Arg Arg Ser Ala Thr Glu
                405                 410                 415

Ser
```

<210> SEQ ID NO 17
<211> LENGTH: 262
<212> TYPE: PRT
<213> ORGANISM: Myxococcus xanthus

<400> SEQUENCE: 17

```
Met Gln Ala Ala Ser Pro Pro His Arg Asp Tyr Gln Thr Leu Arg Val
  1               5                  10                  15

Arg Phe Glu Ala Gln Thr Cys Phe Leu Gln Leu His Arg Pro Asp Ala
               20                  25                  30

Asp Asn Thr Ile Ser Arg Thr Leu Ile Asp Glu Cys Gln Gln Val Leu
           35                  40                  45

Thr Leu Cys Glu Glu His Ala Thr Thr Val Val Leu Glu Gly Leu Pro
    50                  55                  60

His Val Phe Cys Met Gly Ala Asp Phe Arg Ala Ile His Asp Arg Val
 65                  70                  75                  80

Asp Asp Gly Arg Arg Glu Gln Gly Asn Ala Glu Gln Leu Tyr Arg Leu
                 85                  90                  95

Trp Leu Gln Leu Ala Thr Gly Pro Tyr Val Thr Val Ala His Val Gln
            100                 105                 110

Gly Lys Ala Asn Ala Gly Gly Leu Gly Phe Val Ser Ala Cys Asp Ile
        115                 120                 125

Val Leu Ala Lys Ala Glu Val Gln Phe Ser Leu Ser Glu Leu Leu Phe
    130                 135                 140

Gly Leu Phe Pro Ala Cys Val Met Pro Phe Leu Ala Arg Arg Ile Gly
145                 150                 155                 160

Ile Gln Arg Ala His Tyr Leu Thr Leu Met Thr Arg Pro Ile Asp Ala
                165                 170                 175

Ala Gln Ala Leu Ser Trp Gly Leu Ala Asp Ala Val Asp Ala Asp Ser
            180                 185                 190

Glu Lys Leu Leu Arg Leu His Leu Arg Arg Leu Arg Cys Leu Ser Lys
        195                 200                 205

Pro Ala Val Thr Gln Tyr Lys Lys Tyr Ala Ser Glu Leu Gly Gly Gln
    210                 215                 220

Leu Leu Ala Ala Met Pro Arg Ala Ile Ser Ala Asn Glu Ala Met Phe
225                 230                 235                 240

Ser Asp Arg Ala Thr Leu Glu Ala Ile His Arg Tyr Val Glu Thr Gly
                245                 250                 255

Arg Leu Pro Trp Glu Ser
            260
```

-continued

<210> SEQ ID NO 18
<211> LENGTH: 256
<212> TYPE: PRT
<213> ORGANISM: Myxococcus xanthus

<400> SEQUENCE: 18

```
Met Gly Ile Met Thr Glu Gly Thr Pro Met Ala Pro Val Val Thr Leu
  1               5                  10                  15

His Glu Val Glu Glu Gly Val Ala Gln Ile Thr Leu Val Asp Arg Glu
             20                  25                  30

Asn Lys Asn Met Phe Ser Glu Gln Leu Val Arg Glu Leu Ile Thr Val
         35                  40                  45

Phe Gly Lys Val Asn Gly Asn Glu Arg Tyr Arg Ala Val Val Leu Thr
     50                  55                  60

Gly Tyr Asp Thr Tyr Phe Ala Leu Gly Gly Thr Lys Ala Gly Leu Leu
 65                  70                  75                  80

Ser Ile Cys Asp Gly Ile Gly Ser Phe Asn Val Thr Asn Phe Tyr Ser
                 85                  90                  95

Leu Ala Leu Glu Cys Asp Ile Pro Val Ile Ser Ala Met Gln Gly His
            100                 105                 110

Gly Val Gly Gly Gly Phe Ala Met Gly Leu Phe Ala Asp Phe Val Val
        115                 120                 125

Leu Ser Arg Glu Ser Val Tyr Thr Thr Asn Phe Met Arg Tyr Gly Phe
    130                 135                 140

Thr Pro Gly Met Gly Ala Thr Tyr Ile Val Pro Lys Arg Leu Gly Tyr
145                 150                 155                 160

Ser Leu Gly His Glu Leu Leu Leu Asn Ala Arg Asn Tyr Arg Gly Ala
                165                 170                 175

Asp Leu Glu Lys Arg Gly Val Pro Phe Pro Val Leu Pro Arg Lys Glu
            180                 185                 190

Val Leu Pro His Ala Tyr Glu Ile Ala Arg Asp Leu Ala Ala Lys Pro
        195                 200                 205

Arg Leu Ser Leu Val Thr Leu Lys Arg His Leu Val Arg Asp Ile Arg
    210                 215                 220

Arg Glu Leu Pro Asp Val Ile Glu Arg Glu Leu Glu Met His Gly Ile
225                 230                 235                 240

Thr Phe His His Asp Asp Val Arg Arg Ile Glu Gln Leu Phe Leu
                245                 250                 255
```

<210> SEQ ID NO 19
<211> LENGTH: 424
<212> TYPE: PRT
<213> ORGANISM: Myxococcus xanthus

<400> SEQUENCE: 19

```
Met Leu Asn Leu Ile Asn Asn His Ala His Gly Tyr Val Val Thr Pro
  1               5                  10                  15

Val Val Leu Ala Cys Asn Asp Ala Gly Leu Phe Glu Leu Leu Arg Gln
             20                  25                  30

Gly Pro Lys Asp Phe Asp Arg Leu Ala Glu Ala Leu Arg Ala Asn Arg
         35                  40                  45

Gly His Leu Arg Val Ala Met Arg Met Phe Glu Ser Leu Gly Trp Val
     50                  55                  60

Arg Arg Asp Ala Asp Asp Val Tyr Ala Val Thr Ala Ala Ala Ala Ala
 65                  70                  75                  80
```

-continued

```
His Arg Ser Phe Pro Arg Glu Ala Gln Ser Leu Phe Ala Leu Pro Met
                85                  90                  95

Asp Arg Tyr Leu Arg Gly Glu Asp Gly Leu Ser Leu Ala Pro Trp Phe
            100                 105                 110

Glu Arg Ser Arg Ala Ser Trp Asp Thr Asp Thr Leu Val Arg Glu
        115                 120                 125

Leu Leu Asp Gly Ala Ile Ile Thr Pro Leu Met Leu Ala Leu Glu Gln
    130                 135                 140

Arg Gly Gly Leu Lys Glu Ala Arg Arg Leu Ser Asp Leu Trp Ser Gly
145                 150                 155                 160

Gly Asp Gly Arg Asp Thr Cys Val Pro Glu Ala Val Gln His Glu Leu
                165                 170                 175

Ala Gly Phe Phe Ser Ala Gln Lys Trp Thr Arg Glu Asp Ala Val Asp
            180                 185                 190

Ala Glu Leu Thr Pro Lys Gly Ala Phe Ile Phe Glu Arg Ala Leu Leu
        195                 200                 205

Phe Ala Ile Val Gly Ser Tyr Arg Pro Met Leu Ala Ser Met Pro Gln
    210                 215                 220

Leu Leu Phe Gly Asp Cys Asp Gln Val Phe Gly Arg Asp Glu Ala Gly
225                 230                 235                 240

His Glu Leu His Leu Asp Arg Thr Leu Asn Val Ile Gly Ser Gly His
                245                 250                 255

Gln His Arg Lys Tyr Phe Ala Glu Leu Glu Lys Leu Ile Ile Thr Val
            260                 265                 270

Phe Asp Ala Glu Asn Leu Ser Ala Gln Pro Arg Tyr Ile Ala Asp Met
        275                 280                 285

Gly Cys Gly Asp Gly Thr Leu Leu Lys Arg Val Tyr Glu Thr Val Leu
    290                 295                 300

Arg His Thr Arg Arg Gly Arg Ala Leu Asp Arg Phe Pro Leu Thr Leu
305                 310                 315                 320

Ile Ala Ala Asp Phe Asn Glu Lys Ala Leu Glu Ala Ala Gly Arg Thr
                325                 330                 335

Leu Ala Gly Leu Glu His Val Ala Leu Arg Ala Asp Val Ala Arg Pro
            340                 345                 350

Asp Arg Leu Ile Glu Asp Leu Arg Ala Arg Gly Leu Ala Glu Pro Glu
        355                 360                 365

Asn Thr Leu His Ile Arg Ser Phe Leu Asp His Asp Arg Pro Tyr Gln
    370                 375                 380

Pro Pro Ala Asp Arg Ala Gly Leu His Ala Arg Ile Pro Phe Asp Ser
385                 390                 395                 400

Val Phe Val Gly Lys Ala Gly Gln Glu Val Val Pro Ala Glu Val Phe
                405                 410                 415

His Ser Leu Val Glu His Leu Glu
            420

<210> SEQ ID NO 20
<211> LENGTH: 19053
<212> TYPE: DNA
<213> ORGANISM: Myxococcus xanthus

<400> SEQUENCE: 20
gtcgacgttg acgtcgcccg gtggcgtgcc gtgtgtcttc ttcgacgcgg aggtgcgcga     60
ggtggcggcg gacggccggc gcgggccgct gttgtcgcgt gagcgcgcgt atgcgccggt    120
```

```
actggcgctg cgtggccagc gcctccatgc ttcggtgtcc ttttcgcccg cgtcgctgat    180
ggctccggtg gaggtgcgcc ggtgcaaggc cctgccaggc acggtgcccg cgtcctggta    240
tcagacggcg cacccggagg ccctgtcctg ggagcgcgtg ggcgcggtgg gcgaatcctg    300
cctcgtggtg ggtgaactcc ggaggggccc tgtcgagggc agctacgccc tggtcggtcg    360
ggagggcggc cccgcgatgt tggtgctggg accccaggct ccggccacct gtgggacgct    420
ggcgcgccgg gcctggcggc acttcgcggc ggccggggtc ctgtccatgg ccgcggccgt    480
cgtcctgtca ggggcgctgt gagacgcgcg gcggggccg taccgccgcg ccagaaacgt    540
gatgcgccgc caggcctcgc ggtccgggca ctgacgcccg gccgctcgg gactcgctca    600 ggcggctccg gtgcttcgcg cggtggagaa cacgagctgt tcctcgctgt ccgccacccg    660
cacggtgagg gtccgctcca cgccggcgag gcccagcggc gtggactgcg ccaggtccga    720
gagcagggag cccgcagcgc gcaggtggaa gccggtggtc cacatgccct ccagctcgcc    780
gaacacggtg cgcagctcgt ccggggcctt gcgttcgtcg atggcgcggc gcaggcgcac    840
catgccgctc acgaagttcc tgcaccgcat gagcgtgttg gggttcttgg agatgacctc    900
cgcgaagctg aagttgccgc cacccgggcg ccactcgctt tcgatgagct gcaggtcctt    960
gccaaggtcg cgcaccgtgg ggtccttctg gaagtaccac ttggcgatct gcgcggcgcg   1020
gctgggtgac aagtcattca gcatgaggct gccttgctcc tgcacctcgc ggaggtaggc   1080
ctcccagatg ggggcgtaga ccgcgcgccg gaactcggcg gaggcgcggg gaagctgctc   1140
gctccagggc agcgcgcggg ccagggcgcg tgagaagcgg acagctcga gcgtctggat   1200 gcggggcacc agggcgcgga acgagtcatc cgccatcttc agctcgagcc gcgtttcgat   1260
ggggtgcttg cccatgtcct cctgcatggt gctgatgacg gtggccgcgt ccttcgcgtc   1320
cagcacgccc cagacgacgg cgtcatccac cgcctgctgc aggtccttgc gcgacagctt   1380 ctttctgccgt ccccacagca tcaggtgcag gccgtagccg aagtcggagg ccacgggggt   1440
gggagagaag cgcgtcatgt ccgccttcag gtccaccacc cactggccgc gggtgcccag   1500
cagcttgtcc tcgtagcccc ggcgtccgag gaacgccatg cgccgggcgc cctggaagtt   1560
ctcctgcgtc acccaggact gcttgctgac gttcttcgcc ttgagcagct cgaacgagcc   1620
cagccccagt gagaagccga tggcctgctg gcgcgtgagc gtggtggcgt gcaggtagtt   1680
gcgcagctcg aactcgctct gctgggcggg gaggctcttc atccacttca gcagctccac   1740
caggttgccc ttgagcaggg actcgtggaa gcgcatcgcg gtgacgtcct ccacgacgac   1800
ctccagcagc gtggaggtct ccgacaggcg caggtattcg tactcgaagc cctcggcgac   1860
ctgcgtgcgg acggcgttct ccagcgactc tgcgacgcgg gccttgaagt cggcccaggc   1920
ctgcggaagg ttggccgggt ccgcaagctg cgggtcgatg ccaaggcgct ccagcaccag   1980
gcccagcacc ttcttctgat tgtcgtccag cttcgccttg ctggccttgt ccaccaggcc   2040
gtccatgatt tccaccgcgg tggtgccctt cttgacgagg tcgcgaagga cgggcccccag   2100 cagcgcttcc agcaactggc ccagttgggc cttcaccgtc gccgggtcca gcagctccac   2160
ggtgatgccc aggccggcgg agagcgcctg ctcatgggac ttcaccttgc gcacggcgac   2220
ctggatgcgg ccggcacggg gacgggagaa gctgagctgg tagtcgtcgg tgagggacac   2280
ccgggcggac aggcccgcct tggcgctggt cttcaacgcg agcagctcgt tgccgcgcag   2340
gaagcccagg cggttgaggt tggtggggaa gatgtccgcc cagttgagct ccagccgtgt   2400
gtggagcgcg ccgcggacat gccacgccac cgcgtccccc gtggtcagct tggccaggtc   2460
ggtggcctgc atcagccgca gctcggacag gtcggagcgc acggcctcac gcatgttctg   2520
```

-continued

```
gcccagcgga tgcgcgcggt agtcgctgag cgtgacggac agctccgtct ggttctcgga      2580
ggcgaggaag acaggctggc cgctcacggc ggccttcacg cgcgcggaca cctggtagcg      2640
catccacccg atgtcactgc ccagcagcag ttggggccgg ggccctggct cggcgctctc      2700
cgggctcggc tcgccgatga tgccgttttc gtccacgtcg cccagcgagt tgaagttccg      2760 gatgacgct tcgccggtgg cttcgaagga gagggtgaag ccgtgcatgg cgagcttggg       2820
cggaaggatt ttctcttccg tgaaggtccc ctgggccagc ggcaccttga tgtcctggtc      2880
ctgcagcttc acgtcgggca ccttgcccgc cacgacgtcg ggaagcttct ccagcagctt      2940
gttgaccact ttcatgcgcg tcccctggg ctgaagcctc ctgcacgtgg gccggaggtc       3000
tcttcgtcgt acgccgttgc ccagctcgga acaaggcgga taccagaaaa gaccggtggt      3060
cagcggacag atgccctgga gggtgggtg ggagccgccc ccgcgcggtg cgtcagggct       3120
cgtcgcccaa tccgtactcc ttgagtttcc gcgcgagcgt gttgcggcca atcgccagca      3180
cgcgggccgc ggcggtgcgg ttgcccttca cggcgtccag cacgcgcagg atgtggcggc      3240
gttcgacctc cgccagtggc agcaggccca catccagggg cgcaggcgca gtcggcgcgt      3300
tgacaccctg agcggctgcg ggaggcggca gggcggcccg gtccacatcg gcaggggca      3360 ggtgctcttc gagaatctcc ccttcacaga gcaccacggc gctctcgata cagttctcca      3420
gctcccgcac gttccgggc cagcggtagc gcttgaggcg ctccaccgcg gcggcgctga      3480
ggcggggcgg cgtcagccgg tgcctccggg cgacggcggc gacgaagtgg cgggcgagcc      3540
gctcgatgtc ctccgcgccg cgctcccgca gcggcggcag caccacctcg accaccttga      3600
tgcggtagta gaggtcctcg cggaagcggc cctcggccac catgcgggcc aggtcccgat      3660
gggtggccgc gacgatgcgc acgtccacct tcacggcctg ggtgcctccc acgcgctcga      3720
actcgcgatc ctggatgacc cgcagcaact gccctgcac cggcaggggc agctcgccaa       3780
tctcgtcgat gaacacggtg ccgccgctgg ccgcttcgaa cttgccgggc acgcggtggt      3840
ccgcgccggt gaaggcgccg cgttcgtggc cgaagagctc gttctcgatg agcgtggcgg      3900
gcagcgccgc gcagtccacc ttgatgaagg gctggtccct gcggggacca ttcacgtgga      3960
cggcacgggc gaacagctcc ttgccgctgc cactctcgcc gcgcagcagc accgtcgcat      4020
cggtgggcgc ggccttgcgc accagtcggt agatggcctg gagctgcggg gactcgccga      4080
tgatgcggtt gaagaagtag cccaccggta cctggggctg ctccttcgcg cgctggagct      4140
cttgatagag gctggtgctc tggagggcgg tgctcacctg cgaggcgatg gcggtgagcc      4200
gctgcgtgtc ctcgtcggtg aagcggtcct cgccgcggcg gttgaggacc tggagcacgc      4260
cgtagagggc gccgtccccg tcgcgcagtg gcacggcgag caggctggtg gtgcggtagc      4320
ccgtcatccg gtcgatgtcc gcgaagaagc gctgctcgcc gcgcgggtcc ggcacgttga      4380
tggcgtgccc cgccttggcg acggtgccgg cgacgccctg gccagcttg acgcgaatct       4440 gggacacctc gggcaggtgc gcggcgcggc tgaacagctc gcggcgggcc gggtccagca      4500
gccagagcgt gccgcggtcc gcttgcaggg tgatggcgat gcggtccatc agcgtctgga      4560
ggaacgcgtc gaggtccacc tccctgccga cgagtcctcc gaagggagg aggacctggg       4620 agacgtccga gggggcttgg ggcatggcgg gcaacggcgg caggacgaag gcggaggccg      4680
caccataaca tccagagggc atgggactgc cccctctcag gccgcgcggc ccagcaccag      4740
ccgctggcct tcgcgtgcgg gctcgcacac ggggaagagg gcgcgggcct gctccgccat      4800
gtcctcgagc atgtcgtcgc cgtgcgccgg gtcatggtgg aacaggcaca gccggcgcgc      4860
```

```
ccccaccagc  ccggccacgc  ccgcggcatc  catcatggtg  gagtggcccc  agcccttctt   4920
cgccacgccc  ttgcggccct  cgtattcgtc  cggcgtgtac  tgcgcatcca  ggcacaggac   4980
gtccgcgccc  tcgaagaggc  ggcccacctc  cggcgcgagc  tcctgcaccc  gcacctccac   5040
gtccgtggcg  tagacgaacg  aatggccatc  cgcctccagg  cggtacgcca  ggcacccctg   5100
cgggtgcggc  acgtcgatgg  gcgtgacgcg  gaaggggccc  acctccacgg  gtcgggcatg   5160
caacgccgag  cggaagtcca  tccgcgagcg  catggtgctc  agcggcaccg  gaaaatgaag   5220
cggctgcatc  tgcgcggcca  actcggactg  gagcgcctgg  gccccattcg  cgcccggacc   5280
gtagagcgtc  agctcggacg  tgggcagcca  ggccggcgtg  aagaagggga  agccctgcac   5340
gtggtcccaa  tgcagatgcg  agaagaagag  cgtggcctcc  tggggcgcgc  cctcgcgcat   5400
catgatttcg  cccagtgcgc  ggatgcccgt  ccccgcatcc  aggatgaggc  ggtggccctg   5460
gctggtcacc  tccacgcagg  ccgtgttgcc  accaatgcgc  gagcccgaca  ccgcgatgct   5520
cccccgaacg  ccatgaaacc  ggacttccat  cgtaagtctc  cttgaatggg  gggcctccgc   5580
ctgggacgcc  ctcatgcccg  gagcctcaga  gcacggggtg  tgccattccc  aaatgcccgg   5640
aatcaggagc  gcgggcctcg  ggctcgtcca  ccggtgctcc  agaatggatc  gcgctcgcct   5700
ggtgcgggcg  atccaaagcg  gtgcaggtcg  cccgcaggac  ggggcggcgg  gcacgtcttc   5760
caacgtccca  cggcagtcct  gtcttcagat  ctctcccgat  gcgggaaggc  gtccaggagg   5820
ttgcacccgg  catcgagcgg  ggctgtgtgt  ttcaagtctt  gtcggagcct  cggacacaac   5880
cgtctgggtt  ctgggaatgc  gccggcttcc  gttcactcca  gagtgattca  atggctctcg   5940
agtgcaggtt  tagcaatcct  cgggccgtaa  ccacgccgtt  gaaggcagtc  acgctctcgt   6000
cacgcttggg  gtgtttccag  cttcaacggt  gtttatcctt  cagggcggtt  tgcttgacac   6060
gctgcctcat  ggaagcgtat  gcaaaacaat  gaaaacggtg  tcgttgccga  gccttagggc   6120
ctccagaacg  ccatcctcgc  ggacccaggc  agccggaatt  tgagacgggg  ctgtcagcgg   6180
tttgaacgca  aggatgcggc  gggggttgtg  gcggcagccc  gaccagaatt  cggttggtgt   6240
gccagttatt  gtcagattct  gagaaatagc  aggctggggg  gaagttgcaa  tgcctgggcc   6300
gcggtgtgct  gagaacgatt  gggttgcatt  gctcgtccgc  gtcaatcacg  agaaagtggc   6360
tgccgctcag  ttggggaaac  acggctacga  gttcttcctg  ccgacgtaca  cgcctcccaa   6420
gtcctcgggt  gtgaaggcga  agcttccgct  cttccccggg  tacctttttct  gtcgttacca   6480 gccgctcaat  ccgtaccgca  tcgtccgggc  gcccggggtc  atccggctgc  tcggaggtga   6540 cgcgggggccg  gaagccgtgc  ccgcacagga  attggaggcc  atccgccggg  tcgcggattc   6600
gggtgtctct  tccaatccct  gtgactatct  gcggtgggg  cagcgcgtgc  gcatcatcga   6660
agggcccctg  acaggtctgg  aaggaagtct  ggtgacgagc  aagagccaac  tccggttcat   6720
tgtctccgtg  gggctgctac  agcgctcggt  gtccgtggag  gtgagcgccg  agcaactgga   6780
accgatcacc  gactgattcc  gcggacatcc  ccttccattc  cttcatcacc  ccgacccgca   6840
gcaaggcttc  agggaccgtg  agtcgttcca  tggacaagag  aattattttc  gacatcgtca   6900
ccagcagtgt  tcgggaggtg  gtacccgaac  tcgaatcaca  tccgttcgag  ccggaggatg   6960
acctggtcgg  actgggcgcg  aactcgctcg  accgcgccga  aatcgtcaac  ctcacgctgg   7020
agaagctggc  gctcaacatc  ccccgggtcg  agctgattga  cgcgaagacc  attggcgggc   7080
tggtggacgt  ccttcacgcg  aggctgtgag  gcgaagccat  ggggccggtc  gggattgaag   7140
ccatgaatgc  ctactgtggc  atcgccaggt  tggatgtgtt  gcagctggcg  acccaccgtg   7200
gcctggacac  ctcccgcttc  gcgaacctgc  tcatggagga  gaagaccgtc  ccgctcccct   7260
```

-continued

```
atgaggaccc tgtcacctac ggcgtgaatg ccgcccggcc catcctggac cagttgaccg   7320
cggcggaacg ggacagcatc gagctgctgg tggcttgcac ggagtcctcg ttcgacttcg   7380
gcaaggccat gagcacctac ctgcaccagc acctggggct gagccgcaac tgccggctca   7440
tcgagctcaa gagcgcctgc tactccgggg tcgccgggct gcagatggcc gtcaacttca   7500
tcctgtccgg cgtgtcgccg ggggccaagg ccctggtggt ggcctccgac ctgtcgcgct   7560
tctccatcgc cgaaggggga gatgcctcca cggaggactg gtccttcgcg gagccgagct   7620
cgggtgcggg cgcggtggcc atgctggtga gcgacacgcc ccgggtgttc cgcgtcgacg   7680
tgggggcgaa cggctactac ggctacgagg tgatggatac ctgccgcccg gtggcggaca   7740
gcgaagcggg agacgcggac ctgtcgctcc tctcgtacct ggactgctgt gagaacgcct   7800
tccgggagta caccgccgc gtccccgcgg cgaactacgc ggagagcttc ggctacctcg   7860
ccttccacac gccgtttggc ggcatggtga agggcgccca ccgcacgatg atgcgcaagt   7920
tctccggcaa gaaccgcggg gacatcgaag cggacttcca gcggcgagtg gccccccggc   7980
tgacctactg ccagcgcgtg gggaacatca tgggcgcgac gatggcgctc tcgctcctcg   8040
ggaccatcga ccacggcgac ttcgccaccg cgaagcggat tggctgcttc tcgtatggct   8100
cggggtgcag ctcggagttc ttcagcggcg tggtgacgga ggaagggcag cagcggcagc   8160
gcgccctggg gctggagaa cgctggggc ccggcagca gctctccatg ccggattacg   8220
acgcgctgct gaaggggaac ggcctggtgc gcttcgggac ccggaacgcc gagctggatt   8280
tcggtgtcgt cggcagcatc cggccgggcg ggtggggcag gcccttgctc ttcttgtcgg   8340
cgattcgtga cttccatcgc gactaccaat ggatttccta gcctcggggc ttcgagcaaa   8400
gccatgtcca gcgtagcgac ggccgtcccc ctgacgcccc gtgacagcgc ggtgagccgc   8460
cggctgcgaa tcaccccag catgtgcggc cagacgtcct tgttcgccgg gcagattggc   8520
gactgggcat gggacaccgt cagccgcctg tgtggcacgg acgtgctgac cgcgaccaac   8580
gcctcaggcg cgcccaccta cctggccttc tattacttcc gcatccgggg cacgcccgcg   8640
ctgcatcccg gcgcgctgcg cttcggcgac acgctggacg tcacgtcgaa ggcgtacaac   8700
ttcggcagcg aatccgtcct gacggtgcac cgcatctgca agacggcgga gggcggcgct   8760
ccggaggcg atgccttcgg ccatgaagag ctgtacgagc agcccagcc aggccgcatc   8820
tacgcggaga ccttcaaccg gtggatcacg cgctcggacg gcaagtcgaa cgagagcctg   8880
atcaagtcct cgcccgtggg gttccagtac gcacacctgc cgctcttgcc ggacgaatac   8940
tcgccgcggc gggcctatgg ggacgcgcgg gcgcggggca cctttcacga tgtggactcc   9000
gcggagtacc ggctgaccgt ggaccgcttc ccgctgcgct acgcggtgga cgtcatccgg   9060
gacgtcaatg gggtggggct catctacttc gcgtcgtatt tctcgatggt ggactgggcc   9120
atctggcagc tggcgaggca ccagggacg agcgagcagg ccttcctgtc gcgcgtggtg   9180
ctggaccagc aactgtgctt cctcggcaac gcggcgctgg acaccacctt cgacatcgac   9240
gtgcagcact gggagcgggt gggcggcggg aagagctgt tcaacgtgaa gatgcgcgag   9300
ggcgcgcagg gccgggacat cgccgtggcg acggtcaagg tgcgcttcga cgccgcttcg   9360
gaaggaggcc gccgtgggtg agccgatgac agacgaacaa atccgcggag tcgtgccacca   9420
gtccatcgtg cgcgtcctgc cccgcgtgcg ctccaacgag attgcgggcc acttgaacct   9480
ccgcgagctg ggcgcggact ccgtggaccg ggtcgagatt ctcacgtcca tcctggacag   9540
cctgcggctg cagaagacgc cactggcgaa gttcgccgac atccgcaaca tcgacgcgct   9600
```

```
ggtggcgttc ctggccggtg aggtcgcggg tggctgagcg ggttcccggc ggagtcggca   9660
tcgaggccat caacgcctac ggcggcgccg cctccattcc ggtgttggac ttgttccggg   9720
gccggcggct ggaccccgaa gcgattctcc aacctgatga tgcaggagcg cggcgtcgcg   9780
ctgccgttcg aggaccccgt caccaacgcg gtcaatgcgg cgcggcccat cctggacgcg   9840
atgtcgcccg aggcccggga gcgcatcgag ctcctggtca cctcgagcga gtccggcgtg   9900
gacttcagca agtccatctc ctcgtatgcg cacgagcacc tggggctgag ccgccactgc   9960
cggttcctgg aggtgaagca ggcgtgttac gccgccaccg gagcgctcca gctagcgctg  10020
ggctacatcg cgtcgggcgt gtcaccgggg gccaaggccc tggtgattgc cacggacgtg  10080
acgctggtgg acgagagcgg tctgtactcc gagccggcga tgggcaccgg cggcgtcgcc  10140
gtgctgctgg gcgacgagcc gcgcgtgatg aagatggacc tgggagcgtt cggcaactac  10200
agctacgacg tcttcgacac cgcgcggccc tcgccggaga ttgatatcgg cgacgtggac  10260
cggtcgctct tcacgtacct ggactgcctc aagcacagct tcgccgcgta tggccgccgg  10320
gtggacggtg tcgacttcgt gtcgacgttc gactacctgg cgatgcacac gccgttcgcc  10380
ggactggtga aggccgggca ccgcaagatg atgcgcgagc tcaccccgtg cgacgtggac  10440
gaaatcgaag cggacttcgg ccggcgcgtg aagccgtcac tgcagtaccc gagtctggtc  10500
gggaacctgt gctccggctc cgtgtacctg agcctgtgca gcatcatcga caccatcaag  10560
cccgagcggt ccgctcgggt gggaatgttc tcctatgggt cgggttgctc gtcggagttc  10620
ttcagcggcg tcatcggccc ggagtccgtg tccgcgctag ctgggttgga catcggtggc  10680
cacctccggg ggcgccgcca gctcacgttc gaccaatatg tcgaattgct gaaagagaac  10740
cttcgctgtc tggttccaac gaagaaccgg gacgtggacg tggagcgcta cctcccgctg  10800
gtgacgcgga cggcgagccg cccgcgcatg ctcgccttgc gaagggtcgt ggactatcat  10860
cgtcagtacg agtgggtgta gctcatacgc cacctccaat tccgacgaat gaacactcct  10920
tccttgacga actggcctgc ccgcctgggc tatctccttg ccgttggcgg cgcatggttc  10980
gcggccgatc aagtcaccaa acagatggcg cgcgacgggg cgaaaaggcc cgtcgcggtc  11040
ttcgatagct ggtggcactt ccactacgtg gagaaccgag cgggtgcgtt cggtctgttc  11100
tccagcttcg gcgaagagtg gcgcatgcct ttcttctacg tcgtgggcgc catctgcatc  11160
gtgttgctga ttggctacta cttctacacg ccgccgacga tgaagctcca gcgctggtcg  11220
ctggcgacga tgattggcgg gcgcgttggg c aactacgtgg accgggtgcg cctgcgctac  11280
gtggtggatt tcgtgtcatg gcacgtgggg gaccgcttct attggccctc cttcaacatc  11340
gcggacacag cggtagtcgt agggggccgcc ctgatgatcc tggagtcgtt ccgcgagccg  11400
cgtcagcagt tgtctcccgg ataggccccg ccatgggtgt gcggtcggcc gccgggccaa  11460
ggactggagt tcatggggac ctcagagcca gttgagccgg accacgcctt gtcaaaacca  11520
ccgcctgtcg cgcccgtcgg cgcccaggca ctgcctcgcg gtccggcaat gcccggcatc  11580
gcgcagttga tgatgttgtt cctgcggccc acggagttcc tggaccgctg cgccgcccgg  11640
tacggtgaca ccttcacccc t caagattccg ggacgccgc cgttcatcca gaccagcgat  11700
cccgccttga tcgaggtcat cttcaagggt gacccggacc tcttcctcgg agggaaggcg  11760
aacaacgggt tgaagccggt ggtgggtgag aactcgctgc tggtgttgga cgggaagcgg  11820
caccggcgtg atcgcaagct catcatgccc accttcctgg gtgaacggat gcatgcgtat  11880
ggctcggtca tccgggacat cgtcaatgcg gcgcttgacc ggtggcccgt cgggaagccg  11940
ttcgcggtcc atgaagagac gcagcagatc atgctggagg tgattctccg ggtgattttc  12000
```

```
ggcctggagg acgcccggac cattgcccag ttccggcacc acgtgcacca ggtgctcaag    12060
ctggccctgt tcctgttccc gaacggggag ggcaagcccg ccgccgaggg cttcgcgcgg    12120
gccgtgggca aggcgtttcc ctccctggac gtgttcgcgt cgctgaaggc gattgacgac    12180
atcatctacc aggagattca ggaccgccgg agccaggaca tcagcgggcg gcaggacgtg    12240
ctctcgctga tgatgcagtc gcactacgac gacggctccg tgatgacgcc ccaggagctg    12300
cgcgacgagc tgatgacgct gctgatggcg ggccacgaga cgagcgcgac catcgccgcg    12360
tggtgcgtct accacctctg ccgtcacccg gatgcgatgg gcaagctgcg tgaggagatc    12420
gcggcccaca cggtggacgg cgtgctgccg ctggcgaaga tcaacgagct gaagttcctg    12480
gatgccgtgg tcaaggagac gatgcgcatc acgcccgtct tcagcctggt ggctcgcgtg    12540
ctcaaggagc cacagaccat tggcggaacg acgtacccgg cgaacgtggt gctgtcgccc    12600
aacatctacg gcacgcacca tcgcgcggac ctgtggggag acccgaaggt ctttcggcca    12660
gagcgtttcc tggaggagcg ggtgaatccg ttccactact tcccttcgg agggggcatc    12720 cggaagtgca tcgggacgag cttcgcctac tacgagatga agatcttcgt ctcggagacg    12780
gtgcgccgca tgcgcttcga taccaggccc ggctaccacg cgaaggtggt gcgccggagc    12840
aacacgctgg cgccgtctca gggcgtgccc atcatcgtcg agtcgcggct gccgagctga    12900
accgcttggc cccaccatct ccagcgcggt gaacatcatg gtcgattcag tgtcgaaaca    12960
ggcacggcgg aaggtgtttc ttttttccgg ccagggcacc cagtcgtact tcatggccaa    13020
ggagctgttt gacacccaga cggggttcaa gcggcagctg ctggagctgg acgagcaatt    13080
caagcagcgg ctggggcact cgattctcga gcgaatctat gacgcgcgcg ccgcgcggtt    13140
ggatccgctc gacgatgtcc tggtgtcctt tcccgccatc ttcatgattg agcatgcgct    13200
ggcgcggctg ctcatcgacc ggggtatcca gccggacgct gtcgtgggcg ccagcatggg    13260
cgaggtggcg gcggcggcga ttgcgggcgc aatctcagtg gacgcggccg tggccctggt    13320
ggcggcgcag gcccagctct ttgcccgtac ggcgccgcgg gcggcatgc tcgcggtgct    13380 tcacgaactg gaagcctgcc ggggcttcac gtccgtcgcg cgggatggcg aggttgcagc    13440
catcaactac ccgtcgaact tcgtccttgc ggcggatgag gcgggcctgg acggattca    13500 gcaggaactc tcccaacgct cggtggcgtt ccaccggttg ccggtgcgct acccctttca    13560
ttcctcgcac ctggacccgc tgagggagga gtaccgaagc cgcgtccgcg cggattcgct    13620
gacgtggccg cgaatcccca tgtactcgtg caccaccgcg aaccgggtgc acgacctgcg    13680
cagcgaccac ttctggaacg tggtccgcgc gcccatccag ctgtacgaca ccgtcctgca    13740
actggagggg cagggcggct gcgacttcat cgacgtcggc cccgccgcgt ccttcgcgac    13800
catcatcaag cgcatcctcg cgcgggactc cacgtcacgg ctcttcccgt tgctcagccc    13860
ttctcccgca tcgaccggga gctcgatggg gtgacgcgga gctgcgcgat gacgaggcg    13920 cccgcaccca gggcgcctgc gcaggtgccg ccgccgccga gctcgccctg ggcgctgcac    13980
acccgaggag cggcgagcgc gccggtgaat gcccgcaagg ccgcgctctt cccggggcag    14040
ggctcgcagg agcgcggcat gggggccgcg ctcttcgacg agttcccgga cctgacggac    14100
atcgccgacg ccatcctggg gtattccatc aagcgtctct gttttggagga cccaggcaag    14160 gagctggcgc agacgcagtt cacccagccg gcgttgtacg tggtgaacgc gctcagctac    14220
ctgaagcggc tgcgtgaagg agcggagcag ccggccttcg tcgcgggcca cagcctgggc    14280
gagtacaacg cgctgctggt cgcggggggcc ttcgacttcg agacgggact gcggctggtg    14340
```

```
aagcggcggg gcgaactcat gagcggcgcg tccggaggga ccatggccgc ggtggtgggc    14400
tgtgatgccg tggccgtgga acaggtcctt cgagaccgtc agctgaccag tctggatatc    14460
gccaacatca actcgcccga ccagattgtg gtctccggac cggcgcagga catcgagcgg    14520
gcacggcagt gtttcgtgga ccgtggcgcg cggtacgttc cgctcaacgt gcgagcgccg    14580
tttcactcgc gctacatgca gccggccgcc agcgagttcg agcgcttcct gtctcagttc    14640
cagtacgcgc cgctccggtg cgtggtcatc tccaacgtca cgggccgacc ttacgctcat    14700
gacaacgtgg tgcaggggct ggctctgcaa ctgcgcagcc cggtgcagtg gacggccacc    14760
gtccgctacc tcctggaaca gggcgtggag gacttcgagg agctgggccc cggccgcgtg    14820
ctgacccgcc tcatcaccgc gaacaagcgg ggcgccccg caccggccac cgccgcgccc    14880
gcgaagtggg cgaatgcctg agccctccgg agcgtcgttg aaatcctcgg ccggtgggcc    14940
gtccggctgc tgagaccact gaatgtccac ctcacctgtg caggagctgg ttgtctcggg    15000
gttcggggtc acctccgcca ttggccaggg ggccgcgtcc ttcacctcgg cgctgctgga    15060
gggcgcggca cggttccggg tgatggagcg gccgggccgt cagcatcagg ccaacgggca    15120
gacgacggcc cacctggggg cggaaatcgc ctcgctggcc gtgcccgaag gcgtcacccc    15180
acaactgtgg cgctcggcca cgttttcggg gcaggccgca ctggtgaccg tccacgaggc    15240
ctggaacgcg gcgcgcctcc aggccgtccc cggacaccgg attggattgg tggtgggggg    15300
caccaacgtg cagcagcgcg acctggtgct gatgcaagac gcctatcgcg agcgggtgcc    15360
ctttctgcgg gcggcctacg ggtcgaccct catggacacc gacctcgtgg gcctctgcac    15420
gcagcagttc gccatccacg ggatgtcctt cacggtggga ggcgcatcgg ccagtggcct    15480
gctggcggtc atccaggccg cggaggcggt gctctcaaga agggtggacg tttgcatcgc    15540
cgtgggggcg ctgatggacg tctcctactg ggaatgccag ggcctgcggg ccatgggcgc    15600
gatgggcacc gaccggttcg cgcgggagcc ggagcgtgcc tgccggccct tcgacgggga    15660
gagtgatggc ttcatctttg gagaggcgtg cggcgccgtg gtggttgagt ctgcggagca    15720
cgctcggcga cgcggggtga ctcctcgcgc atcctgtcg ggctgggcca tgcagttgga    15780
cgcgagccgc ggcccgttgt cgtccatcga agggagtcg caggtgattg gggctgcgct    15840
gcggcacgcg gacctcgcgc cggagcgggt ggactacgtg aatcctcacg gcagcggttc    15900
gcgtcagggg gatgccatcg agctgggggc cttgaaggcg tgcggcctga cgcacgcccg    15960
ggtcaacacc acgaagtcca tcaccgggca tggcctgtcc tcggcgggtg ccgtggggct    16020
catcgccacg ctggtccagt tggagcaggg ccggctgcac ccgtccttga acctggtgga    16080
cccgattgat tcatcgttcc gctggtgggg ggccaccgcg gaggcccagt ccctccagaa    16140
cgcgctggtg ctcgcctacg gcttcggcgg catcaacacc gctgtcgccg tgcgccggag    16200
cgccacggag agctgacacg cccatgcaag ccgcttcccc tccgcaccgc gactaccaga    16260
cgctccgggt ccgcttcgag gcgcagacct gttttctcca gctccaccgg ccggatgcgg    16320
acaacaccat cagccgcacg ctgattgacg agtgccagca ggtgctcacg ttatgtgagg    16380
agcacgccac cacggtggtg ctcgaaggcc tgccacacgt gttctgcatg ggcgcggatt    16440
ttcgagccat ccacgaccgg gtcgacgacg gccgccggga gcaaggcaac gcggagcagc    16500
tgtaccggct gtggctgcaa ctggcgacag gcccctacgt gacggtcgcc catgtgcagg    16560
gcaaggccaa cgcgggcggc ctgggcttcg tcgccgcgtg cgacatcgtg ctggcaaagg    16620
cggaggtcca gttcagtctc tccgagctgc tgttcgggct gttccccgcc tgcgtgatgc    16680
cgttcctcgc ccggcgaatc ggcatccagc gggcgcacta cctgacgctg atgacgcggc    16740
```

-continued

| | |
|---|---|
| ccatcgacgc ggcccaggcg ctgagctggg ggttggcgga cgcggtggac gccgatagcg | 16800 |
| agaagctgtt gcggctccac ttgcgcaggc tgcggtgcct gtcgaagcca gcggtgaccc | 16860 |
| agtacaagaa gtacgcctcc gagctgggcg ccagctgct cgcggccatg ccccgggcca | 16920 |
| tctccgccaa tgaggcgatg ttctccgacc gcgccacgct ggaagccatc catcgctacg | 16980 |
| tggagacagg ccgactccca tgggaatcat gacggaagga acgccaatgg cgccggtggt | 17040 |
| cacgctccat gaggtggagg agggggtggc gcagatcacc ctggtggatc gcgagaacaa | 17100 |
| gaacatgttc agcgagcagc tcgtgcgcga gctcatcacc gtgttcggca aggtgaatgg | 17160 |
| aaacgagcgc taccgcgcgg tggtgctcac cggctacgac acctacttcg cgctcggcgg | 17220 |
| gaccaaggcc ggcctgctgt ccatctgcga cggcatcggc tccttcaacg tcaccaactt | 17280 |
| ctacagcctc gcgctggagt gcgacatccc ggtgatttcc gccatgcagg acatggcgt | 17340 |
| aggcggcggg ttcgcgatgg ggctgttcgc ggacttcgtg gtcctgagcc gggagagcgt | 17400 |
| ctacacgacg aacttcatgc gctacggctt cacgccgggg atgggcgcca cgtacatcgt | 17460 |
| gccgaagcgg ctgggggtact cgctcgggca tgagctcctg ctcaacgcca ggaactaccg | 17520 |
| cggcgccgac ctggagaagc ggggcgtgcc ttttccggtg ttgccgcgca ggaagtctt | 17580 |
| gccccacgcc tacgagattg cgagggacct ggccgcgaaa cctcggctgt cgctcgtgac | 17640 |
| gctcaagcgg cacctggttc gcgacatccg ccgagagctt ccggacgtca tcgagcgtga | 17700 |
| gctggagatg cacggcatca ccttccatca cgacgacgtg aggaggcgca tcgagcagct | 17760 |
| gttcctctga ggcgcgcccc tatgttgaac ctgatcaaca accacgcaca cggttatgtg | 17820 |
| gtcacgcccg tggtcctggc ctgcaacgac gctggcctgt tcgaactcct gcggcaggga | 17880 |
| ccgaaggact tcgaccggtt ggcggaggca ttgcgtgcca accggggaca tctgcgcgtc | 17940 |
| gcgatgagga tgttcgaatc gctcggctgg gttcgccgcg acgcggatga cgtgtacgcg | 18000 |
| gtgacggcg cggcggccgc gcatcggtcc ttcccccgcg aggcgcagtc gctcttcgcg | 18060 |
| ctgcccatgg accggtacct cgcgcgggag gacggcctgt ccctggcgcc gtggttcgag | 18120 |
| cgctctcggg cgtcgtggga taccgatgac acgctggtgc gcgagctgct cgacggcgcc | 18180 |
| atcatcacgc cgctgatgct cgcgctggag cagcgtgggg gcctcaagga ggcgaggcgt | 18240 |
| ctgtccgacc tgtggtccgg ggggatgga agggacacgt gcgtccccga ggccgtccaa | 18300 |
| cacgagctgg ccgggttctt ctccgcgcag aagtggacgc gtgaggacgc cgtcgacgcg | 18360 |
| gagctcacgc ccaagggcgc cttcatcttc gagcgggcat tgctcttcgc catcgtcggc | 18420 |
| tcgtaccggc cgatgctggc cagcatgccg cagctgctct tcggtgactg cgaccaggtc | 18480 |
| ttcgggcggg acgaagcggg ccacgaactg cacctggacc gaaccctcaa cgtgattggg | 18540 |
| agcggccacc agcaccggaa gtacttcgcg gagctggaga agctcatcat caccgtcttc | 18600 |
| gatgccgaga acctgtcggc acagccgcgc tacatcgcgg acatggggtg cggtgacggc | 18660 |
| acgctcctga agcgggtgta tgaaacggtg cttcggcaca cgcggcgggg aagggcgctc | 18720 |
| gaccggtttc cgctcacgct catcgccgcg gacttcaacg agaaggcgct cgaagccgct | 18780 |
| gggcggacgc tggccgggtt ggagcacgtt gccttgcgcg cggacgtggc gcggccggac | 18840 |
| cgtctcatcg aggacctgcg ggcgcgcggg ctagccgagc ctgagaatac gctgcacatc | 18900 |
| cgctcgtttc tcgaccacga ccgtccctac cagcctcccg cggacagggc ggggctccac | 18960 |
| gcccggattc cgttcgattc ggtgttcgtg ggcaaggcgg gccaggaggt ggttccggcg | 19020 |
| gaggtgttcc acagcctggt ggagcacctc gag | 19053 |

DNA ENCODING A POLYPEPTIDE REQUIRED FOR BIOSYNTHESIS OF TA ANTIBIOTIC

CROSS REFERENCES TO RELATED APPLICATIONS

This is a continuation-in-part of U.S. patent application Ser. No. 09/240,537, filed Jan. 29, 1999, now abandoned.

BACKGROUND OF THE INVENTION

Polyketides constitute a large and highly diverse group of secondary metabolites synthesized by bacteria, fungi and plants, with a broad range of biological activities and medical applications. They include anti-cancer agents (Daunorubicin), antibiotics (tetracyclines, erythromycin etc.), immunosuppressants (macrolide FK506) and compounds with mycotoxic activity (aflatoxins, ochratoxins, ergochromes, patulin etc.). Polyketides are synthesized by repetitive condensations of acetate or propionate monomers in a similar way to that of fatty acid biosynthesis. Structural diversity of polyketides is achieved through different thioester primers, varying chain extension units used by the polyketide synthases (PKSs), and variations in the stereochemistry and the degree of reduction of intermediates. Diversity is also achieved by subsequent processing, such as alkylations, oxidations, O-methylations, glycosylations and cyclizations. Genetic studies indicated that gene organization of functional units and motif patterns of various PKSs are similar. This similarity was used to identify and obtain new PKS systems in both gram negative and gram positive bacteria.

PKS systems are classified into two types: type I PKSs are large, multifunctional enzymes, containing a separate site for each condensation or modification step. These represent "modular PKSs" in which the functional domains encoded by the DNA sequence are usually ordered parallel to the sequence of reactions carried out on the growing polyketide chain. Type II PKSs are systems made up of individual enzymes, in which each catalytic site is used repeatedly during the biosynthetic process.

Genetic studies on prokaryotic PKSs have focused on gram positive microorganisms, particularly on actinomycetes. Myxobacteria are gram negative bacteria that produce a large number of secondary metabolites, including polyketides. *Myxococcus xanthus* produces TA (Rosenberg, et al., 1973; Rosenberg. et al., 1984), which is an antibacterial antibiotic.

The polyketide antibiotic Tel-Aviv (hereinafter TA) (Rosenberg, et al., 1973) is synthesized by the gram negative bacterium *Myxococcus xanthus* in a unique multi-step process incorporating a glycine molecule into the polyketide carbon chain, which is elongated through the condensation of 11 acetate molecules by a type I polyketide synthase PKSs).

The antibiotic TA was crystallized and its chemical properties were determined. It is a macrocyclic polyketide synthesized through the incorporation of acetate, methionine, and glycine. It inhibits cell wall synthesis by interfering with the polymerization of the lipid-disaccharide-pentapeptide and its ability to adhere avidly to tissues and inorganic surfaces makes it potentially useful in a wide range of clinical applications, such as treating gingivitis.

A growing interest in the study of PKS systems and peptide synthetase systems stems from the need to develop new potent biologically active compounds. The use of combinatorial genetics in both systems (PKS and peptide synthetase) separately has led to the production of new polyketides and new peptides.

It would therefore by useful to be able to generate new biological agents from secondary metabolites of the antibiotic TA.

SUMMARY OF THE INVENTION

According to the present invention, there is provided a purified, isolated and cloned DNA sequence partially encoding a functional portion of a polypeptide component required for the synthesis of antibiotic TA. Also provided are purified, isolated and cloned DNA sequences encoding a polypeptide component required for postmodification of antibiotic TA and encoding a gene product involved in the regulation of the biosynthesis of antibiotic TA. A purified, isolated and cloned DNA sequence having a DNA sequence (Seq. ID NO:2 and 20) encoding a polypeptide component required for encoding the TA gene cluster and any mutations thereof is provided. Also provided are methods of using the TA gene cluster and any mutations thereof is provided. Also provided are methods of using the TA genes for combinatorial genetics and of using the TA genes encoding for synthesis and modification or regulation of antibiotic TA.

DESCRIPTION OF THE DRAWING

Other advantages of the present invention will be readily appreciated as the same becomes better understood by reference to the following detailed description when considered in connection with the accompanying drawing wherein.

DETAILED DESCRIPTION OF THE INVENTION

Figure 1:
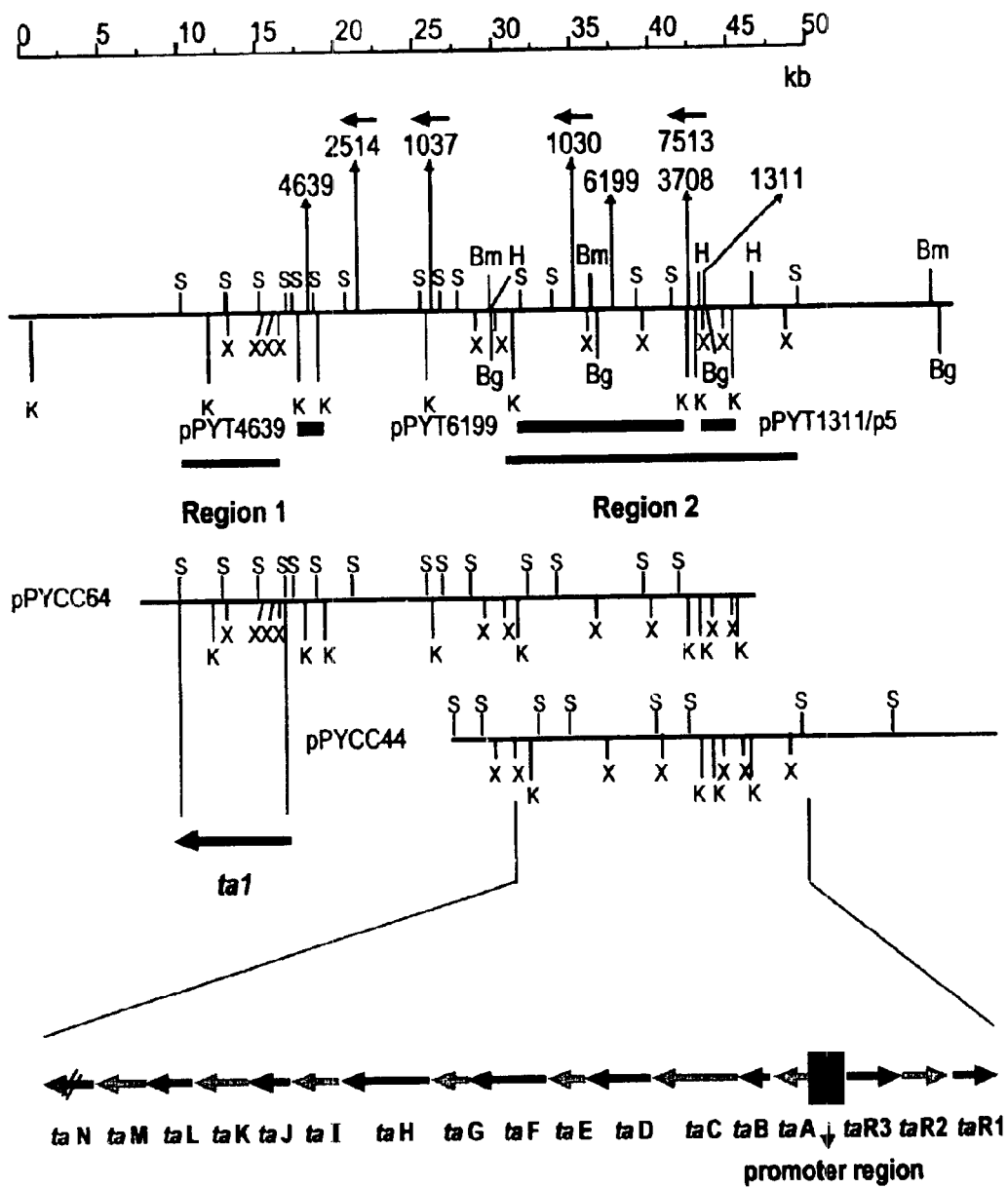
FIG. 1 shows the physical maps of the DNA regions involved in TA synthesis.

The present invention consists of DNA sequences isolated from *Myxococcus xanthus* TA gene cluster of at least 42 kb, encoding peptides involved in TA production, as best shown in Seq ID NOs: 1 and 3–19. The TA gene cluster has been purified, isolated and cloned. The purification, isolation and cloning was done according to the methods described in Marshak et al, "Strategies for Protein Purification and Characterization. A laboratory course manual" CSHL Press, 1966.

A DNA fragment of at least 42 kb (FIG. 1), encoding genes involved in TA production in *Myxococus xanthus* has been identified, cloned and analyzed. These steps were done in accordance with Marshak et al, "Strategies for Protein Purification and Characterization. A laboratory course manual" CSHL Press, 1966. This fragment consists a large region (designated Region 2) of about 20 kb, encoding the polypeptides TaA, TaB, TaC, TaD, TaE, TaF, TaG, TaH, TaI, TaJ, TaK, TaL, TaM, TaN, TaR3, TaR2 and TaR1, which are responsible for the regulation of the post-modification of TA. An additional fragment (designated Region 1) of approximately 8–10 kb is located 10–20 kb downstream of the post modification region, encoding the Ta1 polypeptide. The Ta1 polypeptide is involved in the incorporation of the glycine into the TA polypeptides chain. This novel polypeptide is made up of a peptide synthetase unit lying between two PKS modules.

The potential of this unique polypeptide in combining the two systems can lead to a new family of compounds, emerging from various combinations which can be utilized for combinatorial genetics. Such utilization can produce, for example, new bioactive agents, new polyketides and new peptides. Additionally, the TA gene cluster can be utilized in a method for the synthesis, modification or regulation of the TA antibiotic.

TABLE 1

Polypeptides encoded by the TA gene cluster of *Myxococcus xanthus*

| SEQ ID NO. | Function |
|---|---|
| 1 | Ta1—synthetase unit and a PKS module |
| 3 | TaR1—a surface layer protein |
| 4 | TaR2—two component system, response regulator |
| 5 | TaR3—two component system, kinase sensor |
| 6 | TaA—NUS-G like transcription antiterminator |
| 7 | TaB—an ACP |
| 8 | TaC—beta-ketoacyl (ACP) synthase III (KAS III FabH) |
| 9 | TaD—membrane associated protein |
| 10 | TaE—an ACP |
| 11 | TaF—beta-ketoacyl (ACP) synthase III (KAS III FabH) |
| 12 | TaG—signal peptidase II (LSPA) |
| 13 | TaH—cytochrome P450 hydroxylase (cP450) |
| 14 | TaI—malonyl CoA (ACPP transacylase (MCT, FabD) |
| 15 | TaJ—malonyl CoA (ACPP transacylase (MCT, FabD) |
| 16 | TaK—3-oxoacyl (ACP) synthase (KAS I, FabB) |
| 17 | TaL—enoyl CoA hydratase |
| 18 | TaM—enoyl CoA hydratase |
| 19 | TaN—O-methyltransferase (fragment) |

PKS—polyketide synthase
ACP—acyl carrier protein

TABLE 2

DNA sequences identified from the TA gene cluster of *Myxococcus xanthus*

| SEQ ID NO. | Description |
|---|---|
| 2 | Nucleotides 1–7178 |
| 20 | Nucleotides 1–19053 |

Mutations imparting defects into the TA gene cluster can be point mutations, deletions or insertions. The mutations can occur within the nucleotide sequence of the allele of the TA gene cluster such that the resulting amino acid sequence of the TA gene cluster product is altered.

In one embodiment of the present invention, the TA gene cluster can be included in a vector or recombinant expression vector. This vector containing the TA gene cluster is able to transform a suitable eucaryotic or procaryotic host cell. A suitable host cell can be determined by one skilled in the art. An example of a suitable cell which can be transformed by the TA gene cluster is an *E. coli* cell.

In another embodiment of the present invention, the a DNA fragment encoding the TA gene cluster can be cloned into a cosmid, as shown in FIG. 1. This DNA fragment contains a large region of about 20 kb, encoding the genes responsible for the regulation and the post-modification of TA. An additional fragment of approximately eight to ten kb is located 10–20 kb downstream of the post-modification region and encodes the enzyme responsible for the incorporation of the glycine into the polyketide chain. The novel polyketide chain is made up of a peptide synthetase unit lying between two PKS modules (See FIG. 1).

The above discussion provides a factual basis for the use of the TA gene cluster. The methods used with and the utility of the present invention can be shown by the following non-limiting examples and accompanying figure.

EXAMPLES

General Methods

Methods:

General methods in molecular biology: Standard molecular biology techniques known in the art and not specifically described are generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) is carried out generally as in *PCR Protocols: A Guide To Methods And Applications*, Academic Press, San Diego, Calif. (1990). Reactions and manipulations involving other nucleic acid techniques, unless stated otherwise, are performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference. In-situ (In-cel) PCR in combination with Flow Cytometry can be used for detection of cells containing specific DNA and mRNA sequences (Testoni et al, 1996, Blood 87:3822.)

Recombinant Protein Purification

Marshak et al, "Strategies for Protein Purification and Characterization. A laboratory course manual." CSHL Press, 1996.

Example 1

Analysis of the TA Gene Cluster by Chromosomal Restriction Map.

Chromosomal DNA of several transposition mutants (ER-2514, ER-1037, ER-1030, ER-1311, ER-7513, ER-3708, ER-4639 and ER-6199; Varon et al., 1992) was extracted, digested with restriction enzymes that cut within the transposon, and analyzed by Southern hybridization with six different probes (originating from TnV and Tn5lac). We used probes designed to hybridize either to the entire transposon, or to its 5' or 3' ends. A chromosomal restriction map of the whole gene cluster was constructed on the basis of these results (FIG. 1). The data refined the transduction map (Varon et al, 1992) and further indicated that all the genes in the cluster are transcribed in the same direction (see FIG. 1).

Preparation of TA-specific Probes

DNA from the TnV mutant ER-4639, ER1311 and ER-6199 was digested with KpnI (does not restrict TnV), self-ligated and transformed into *E. coli* XL1-Blue MR using the transposon-derived kanamycin resistance for selection. Tranformant clones pPYT4639, pPYT1311/p5 and pPYT6199 carried a 1.5 kb, 2.3 kb and a 11.2 kb fragment, respectively (see FIG. 1).

Cloning of a *M. Xanthus* DNA Region Encoding Genes Involved in TA Biosynthesis.

A library of *M. xanthus* ER-15 was constructed in the cosmid vector SUPERCOS-1 and screened using specific TA probes obtained from transposition mutants (ER-4639, ER-1311 and ER-6199, see map) that contain a TnV transposon. Seventy four recombinant cosmids that carried genes required for TA production were identified through colony hybridization. The cosmids, pPYCC64 and pPYCC44, which hybridized to these probes were further characterized through restriction analysis (see FIG. 1) and sub cloned for sequencing.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

References

1. Rosenberg, E., Vaks, B. and Zuckerberg. A. Bactericidal action of an antibiotic produced by *Myxococcus xanthus*. Antimicrob. Agents. Chemother. 4:507–513 (1973).

2. Rosenberg, E., Porter, J. M., Nathan, P. N., Manor, A. and Varon, M. Antibiotic TA: an adherent antibiotic. Bio/Technology. 2:796–799 (1984).

3. Varon et al., Mutation and mapping of genes involved in production of the antibiotic TA in *micrococcus xanthus*. Antimicrob. Agents Chemother. 36:2316–2321 (1992).

4. Marshak et al, "Strategies for Protein Purification and Characterization. A laboratory course manual." CSHL Press, 1996.

5. Testoni et al, 1996, Blood 87:3822.

6. *PCR Protocols: A Guide To Methods And Applications*, Academic Press, San Diego, Calif. (1990).

7. Sambrook et al., *Molecular Cloning: A Laboratory Manual*, Cold Springs Harbor Laboratory, New York (1989, 1992).

8. Ausubel et al., *Current Protocols in Molecular Biology*, John Wiley and Sons, Baltimore, Md. (1989).

What is claimed is:

1. An isolated DNA sequence comprising a polynucleotide encoding a polypeptide set forth in SEQ ID No: 1, wherein said polypeptide is required for the synthesis of antibiotic TA.

2. A vector comprising the isolated DNA sequence according to claim 1.

3. A vector, according to claim 2, further comprising a promoter sequence operatively linked to the isolated DNA sequence.

4. A cosmid containing the DNA sequence according to claim 1.

5. A host cell transformed with the vector according to claim 3.

6. An *E. coli* host cell transformed with the vector according to claim 3.

7. A method of making a polypeptide comprising the following steps:
   culturing a host cell according to claim 5, under such conditions that the encoded polypeptide is expressed, and
   isolating said encoded polypeptide.

* * * * *